United States Patent
Tada et al.

(10) Patent No.: US 12,185,624 B2
(45) Date of Patent: Dec. 31, 2024

(54) ORGANIC ELECTROLUMINESCENT ELEMENT

(71) Applicant: NIPPON STEEL CHEMICAL & MATERIAL CO., LTD., Tokyo (JP)

(72) Inventors: Masashi Tada, Tokyo (JP); Yuta Sagara, Tokyo (JP); Munetomo Inoue, Tokyo (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 990 days.

(21) Appl. No.: 16/966,963

(22) PCT Filed: Feb. 13, 2019

(86) PCT No.: PCT/JP2019/004976
§ 371 (c)(1),
(2) Date: Aug. 3, 2020

(87) PCT Pub. No.: WO2019/171891
PCT Pub. Date: Sep. 12, 2019

(65) Prior Publication Data
US 2020/0411770 A1 Dec. 31, 2020

(30) Foreign Application Priority Data
Mar. 7, 2018 (JP) .................... 2018-041153

(51) Int. Cl.
*H10K 85/60* (2023.01)
*C07D 487/04* (2006.01)
*C09K 11/06* (2006.01)
*H10K 50/11* (2023.01)
*H10K 101/00* (2023.01)
*H10K 101/20* (2023.01)

(52) U.S. Cl.
CPC ....... *H10K 85/6572* (2023.02); *C07D 487/04* (2013.01); *C09K 11/06* (2013.01);
(Continued)

(58) Field of Classification Search
CPC ................................................ H10K 2101/20
See application file for complete search history.

(56) References Cited

U.S. PATENT DOCUMENTS

2010/0295444 A1 11/2010 Kuma et al.
2012/0241732 A1 9/2012 Endo et al.
(Continued)

FOREIGN PATENT DOCUMENTS

| DE | 102016122122 A1 * | 5/2017 | ........... C07D 401/04 |
| DE | 102016113277 A1 | 1/2018 | |

(Continued)

OTHER PUBLICATIONS

International Preliminary Report on Patentability for International Application No. PCT/JP2019/004976, dated May 26, 2020.
(Continued)

*Primary Examiner* — Sean M DeGuire
(74) *Attorney, Agent, or Firm* — Birch, Stewart, Kolasch & Birch, LLP

(57) ABSTRACT

Provided is a thermally activated delayed fluorescent blue light-emitting organic EL device having high luminous efficiency and a long lifetime. The organic electroluminescent device includes one or more light-emitting layers between an anode and a cathode opposite to each other, wherein at least one of the light-emitting layers contains an indolocarbazole compound represented by the following general formula (1), which serves as a thermally activated delayed fluorescent light-emitting material, and a carbazole compound serving as a host material, and a substituent $Ar^2$ with which a N atom in the indolocarbazole ring compound is substituted has at least one fluorine atom.

(Continued)

(56) References Cited

U.S. PATENT DOCUMENTS

| | | | |
|---|---|---|---|
| 2015/0021575 A1 | 1/2015 | Takada | |
| 2016/0087227 A1* | 3/2016 | Kim | H10K 85/6565 257/40 |
| 2018/0212158 A1* | 7/2018 | Aspuru-Guzik | C07D 471/04 |
| 2018/0366656 A1 | 12/2018 | Tada et al. | |

FOREIGN PATENT DOCUMENTS

| | | |
|---|---|---|
| WO | WO 2016/017684 A1 | 2/2016 |
| WO | WO 2017/115596 A1 | 7/2017 |
| WO | WO 2018/224421 A1 | 12/2018 |

OTHER PUBLICATIONS

Li et al., "Red phosphorescent organic light-emitting diodes based on a novel host material with thermally activated delayed fluorescent properties," Sci. China Chem. (Jun. 2016), vol. 59, No. 6, pp. 684-691.

Zhang et al., "Towards ideal electrophosphorescent devices with low dopant concentrations: the key role of triplet up-conversion," J. Mater. Chem, C (2014), vol. 2, pp. 8983-8989.

\* cited by examiner

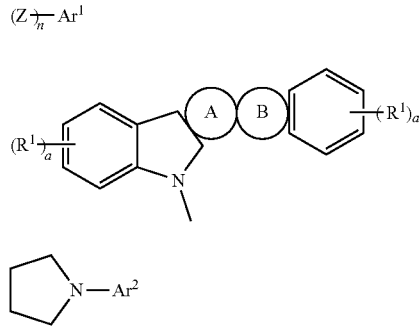

10 Claims, 1 Drawing Sheet

(52) U.S. Cl.
CPC .... *H10K 85/654* (2023.02); *C09K 2211/1018* (2013.01); *H10K 50/11* (2023.02); *H10K 2101/20* (2023.02); *H10K 2101/90* (2023.02)

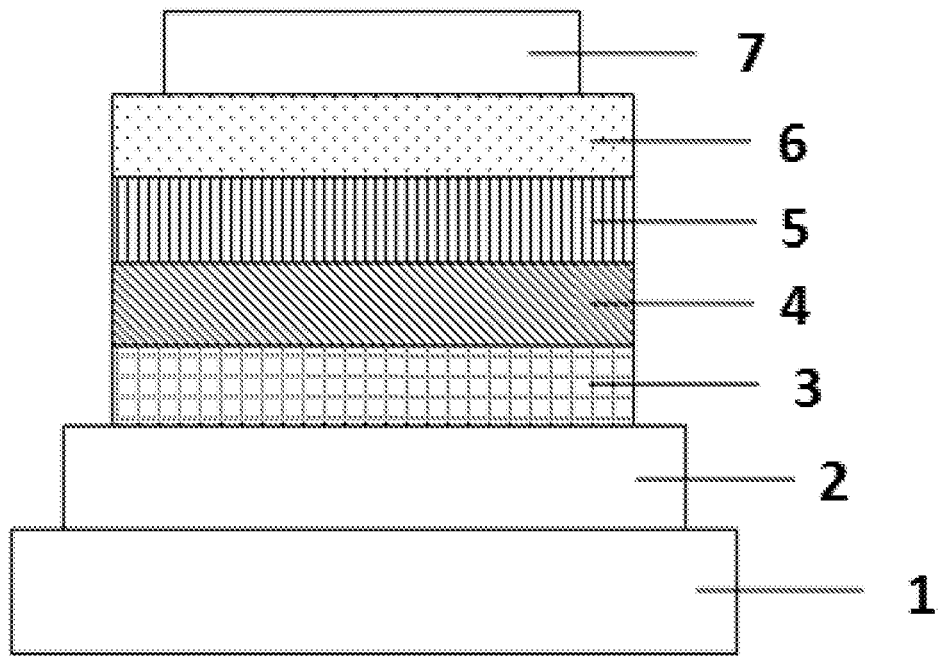

ORGANIC ELECTROLUMINESCENT ELEMENT

TECHNICAL FIELD

The present invention relates to an organic electroluminescent device (referred to as organic EL device).

BACKGROUND ART

When a voltage is applied to an organic EL device, a hole is injected from an anode into a light-emitting layer, and an electron is injected from a cathode into the layer. Then, in the light-emitting layer, the hole and the electron thus injected recombine to produce an exciton. At this time, according to the statistical law of electron spins, singlet excitons and triplet excitons are produced at a ratio of 1:3. The internal quantum efficiency of a fluorescent emission-type organic EL device using light emission by a singlet exciton is said to be at most 25%. Meanwhile, it has been known that the internal quantum efficiency of a phosphorescent emission-type organic EL device using light emission by a triplet exciton can be improved to 100% when intersystem crossing from a singlet exciton is efficiently performed.

In recent years, a technology for the lengthening of the lifetime of a phosphorescent organic EL device has been advancing, and has started to be applied to the display of a cellular phone or the like. With regard to a blue organic EL device, however, a practical phosphorescent emission-type organic EL device has not been developed, and hence the development of a blue organic EL device having high efficiency and a long lifetime has been required.

Further, a high-efficiency delayed fluorescent organic EL device utilizing delayed fluorescence has been recently developed. In, for example, Patent Literature 1, there is a disclosure of an organic EL device utilizing a triplet-triplet fusion (TTF) mechanism serving as one of the delayed fluorescence mechanisms. The TTF mechanism utilizes a phenomenon in which a singlet exciton is produced by collision between two triplet excitons, and is considered to be capable of improving internal quantum efficiency to 40% in theory. However, a further improvement in efficiency has been required because the efficiency of the device is lower than that of a phosphorescent light-emitting organic EL device.

Meanwhile, in Patent Literature 2, there is a disclosure of an organic EL device utilizing a thermally activated delayed fluorescence (TADF) mechanism. The TADF mechanism utilizes a phenomenon in which inverse intersystem crossing from a triplet exciton to a singlet exciton occurs in a material having a small energy difference between a singlet level and a triplet level, and is considered to be capable of improving internal quantum efficiency to 100% in theory. However, a further improvement in lifetime characteristic has been required as in a phosphorescent light-emitting device.

Such delayed fluorescent organic EL device has a feature in that its luminous efficiency is high, but a further improvement of the device has been required.

CITATION LIST

Patent Literature

[PTL 1] WO 2010/134350 A1
[PTL 2] WO 2011/070963 A1
[PTL 3] JP 2015-20953 A

In Patent Literature 2, there is a disclosure of the use of an indolocarbazole compound as a thermally activated delayed fluorescent light-emitting material (TADF material).

In Patent Literature 3, there is a disclosure of such an indolocarbazole compound as represented below as a material for a phosphorescent light-emitting layer in an organic electroluminescent device.

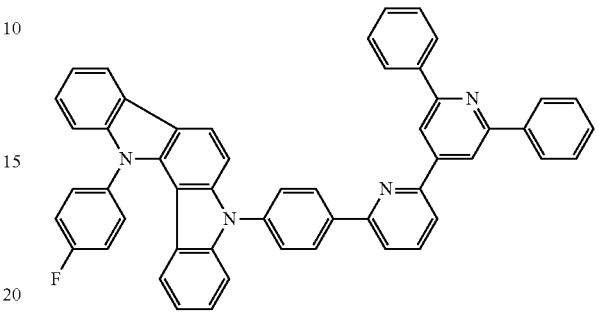

SUMMARY OF INVENTION

In order to apply an organic EL device to a display device, such as a flat panel display, or a light source, the luminous efficiency of the device needs to be improved, and at the same time, stability at the time of its driving needs to be sufficiently secured. In view of the above-mentioned present circumstances, an object of the present invention is to provide a practically useful organic EL device having high efficiency and high driving stability.

According to one embodiment of the present invention, there is provided an organic electroluminescent device, including one or more light-emitting layers between an anode and a cathode opposite to each other, wherein at least one of the light-emitting layers contains a compound represented by the following general formula (1) as a thermally activated delayed fluorescent light-emitting material:

(1)

(1a)

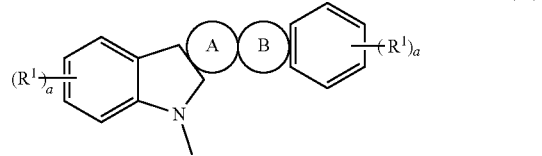

(1b)

(1c)

where:
Z represents a fused aromatic heterocycle represented by the formula (1a), a ring A is an aromatic hydrocarbon ring represented by the formula (1b), a ring B is a heterocycle represented by the formula (1c), and the ring A and the ring B are each fused with an adjacent ring at arbitrary positions;

Ar¹ represents a substituted or unsubstituted aromatic hydrocarbon group having 6 to 30 carbon atoms, a substituted or unsubstituted aromatic heterocyclic group having 3 to 17 carbon atoms, or a linked aromatic group formed by linking 2 to 6 aromatic rings of aromatic groups each selected from the aromatic hydrocarbon group and the aromatic heterocyclic group;

Ar² represents a group having at least one fluorine atom, and represents an aromatic hydrocarbon group having 6 to 30 carbon atoms, an aromatic heterocyclic group having 3 to 17 carbon atoms, or a linked aromatic group formed by linking 2 to 6 aromatic rings of aromatic groups each selected from the aromatic hydrocarbon group and the aromatic heterocyclic group;

R¹s each independently represent an aliphatic hydrocarbon group having 1 to 10 carbon atoms, a substituted or unsubstituted diarylamino group having 12 to 44 carbon atoms, a substituted or unsubstituted aromatic hydrocarbon group having 6 to 18 carbon atoms, or a substituted or unsubstituted aromatic heterocyclic group having 3 to 17 carbon atoms, n represents an integer of 1 or 2, a represents an integer of from 0 to 4, and b represents an integer of from 0 to 2; and when Ar¹ or Ar² represents a linked aromatic group, the aromatic rings to be linked may be identical to or different from each other, and the linked aromatic group may be linear or branched.

Ar² in the general formula (1) preferably represents a phenyl group or biphenyl group having at least one fluorine atom. Such phenyl group or biphenyl group may have a substituent, and preferably has 1 to 6 fluorine atoms.

A preferred mode of the general formula (1) is a mode represented by any one of the following general formulae (3) to (8). In the general formulae (3) to (8), the same symbols as those of the general formula (1) have the same meaning.

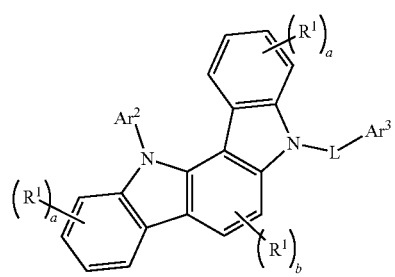

(3)

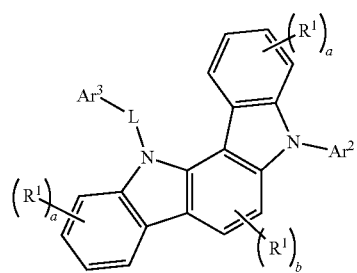

(4)

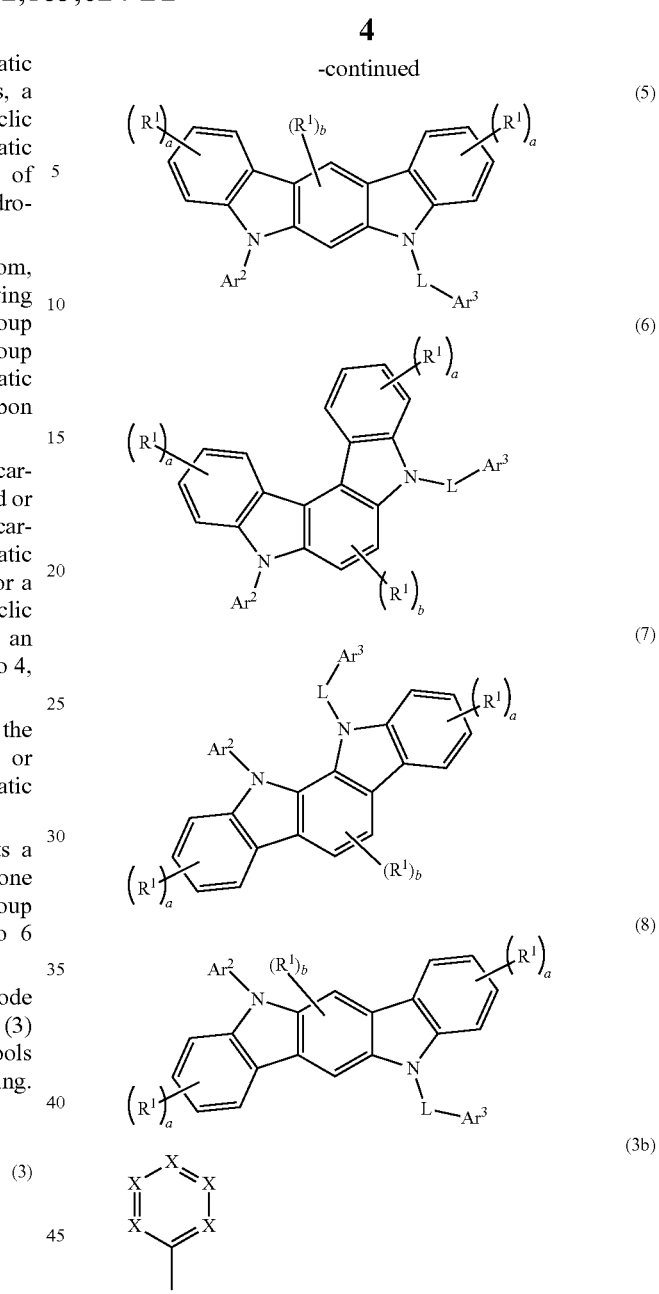

In the formulae, Ar² and R¹ are identical in meaning to those of the general formula (1) (including formulae (1a), (1b), and (1c)).

L represents a single bond, a substituted or unsubstituted aromatic hydrocarbon group having 6 to 12 carbon atoms, or a substituted or unsubstituted aromatic heterocyclic group having 3 to 10 carbon atoms, preferably a substituted or unsubstituted aromatic hydrocarbon group having 6 to 12 carbon atoms.

Ar³ represents a heterocyclic group represented by the general formula (3b), Xs each represent CR² or N, and at least one of Xs represents N, R² represents hydrogen, an aliphatic hydrocarbon group having 1 to 10 carbon atoms, a substituted or unsubstituted aromatic hydrocarbon group having 6 to 18 carbon atoms, a substituted or unsubstituted aromatic heterocyclic group having 3 to 10 carbon atoms, or a linked aromatic group formed by linking 2 to 4 aromatic rings of aromatic groups each selected from the aromatic hydrocarbon group and the aromatic heterocyclic group, and when Ar³ represents a linked aromatic group, the aromatic rings to be linked may be identical to or different from each other, and the linked aromatic group may be linear or branched, a represents an integer of from 0 to 4, and b represents an integer of from 0 to 2.

It is preferred that a difference between an excited singlet energy (S1) and an excited triplet energy (T1) of the thermally activated delayed fluorescent light-emitting material be 0.2 eV or less.

The organic EL device of the present invention preferably includes a host material in the light-emitting layer containing the thermally activated delayed fluorescent material. In addition, the light-emitting layer may contain two or more kinds of host materials.

As the host material, there is given a compound represented by the following general formula (9):

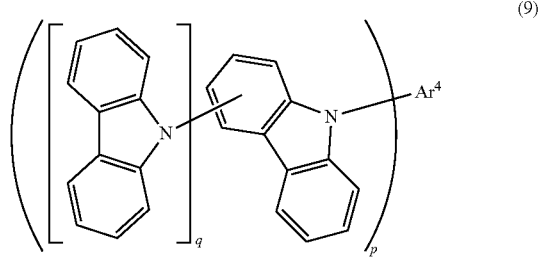

(9)

where Ar⁴ represents a p-valent group, which may have a substituent and is produced from benzene, a nitrogen-containing six-membered heterocyclic compound, dibenzofuran, dibenzothiophene, carbazole, carborane, or a linked compound obtained by linking 2 to 4 of the compounds, p represents an integer of 1 or 2, and q represents an integer of from 0 to 4, and when Ar⁴ represents a p-valent group produced from benzene, q represents an integer of from 1 to 4.

The host material may include two or more kinds of compounds each represented by the general formula (9).

It is preferred that the host material have an excited triplet energy (T1) larger than an excited singlet energy (S1) of the thermally activated delayed fluorescent material.

It is preferred that the compound represented by the general formula (9) be incorporated into a layer adjacent to the light-emitting layer.

The organic EL device of the present invention is a delayed fluorescent organic EL device having high luminous efficiency and a long lifetime because the device contains a specific thermally activated delayed fluorescent material in a light-emitting layer thereof.

BRIEF DESCRIPTION OF DRAWINGS

FIG. 1 is a schematic sectional view for illustrating an example of an organic EL device.

DESCRIPTION OF EMBODIMENTS

An organic EL device of the present invention includes one or more light-emitting layers between an anode and a cathode opposite to each other, and at least one of the light-emitting layers contains a compound represented by the general formula (1) as a TADF material. The organic EL device has an organic layer formed of a plurality of layers between the anode and the cathode opposite to each other, and at least one of the plurality of layers is a light-emitting layer. A host material may be incorporated into the light-emitting layer as required, and a preferred host material is a compound represented by the general formula (9). The incorporation of the compound as a TADF material allows the light-emitting layer to emit thermally activated delayed fluorescence.

The general formula (1) is described.

Z represents a fused aromatic heterocyclic group represented by the formula (1a), a ring A is an aromatic hydrocarbon ring represented by the formula (1b), a ring B is a heterocycle represented by the formula (1c), and the ring A and the ring B are each fused with an adjacent ring at arbitrary positions. n represents an integer of 1 or 2, and preferably represents an integer of 1.

In the general formula (1), Ar¹ represents an n-valent group.

Ar¹ represents a substituted or unsubstituted aromatic hydrocarbon group having 6 to 30 carbon atoms, a substituted or unsubstituted aromatic heterocyclic group having 3 to 17 carbon atoms, or a linked aromatic group formed by linking 2 to 6 aromatic rings of aromatic groups each selected from the aromatic hydrocarbon group and the aromatic heterocyclic group. Ar¹ preferably represents a substituted or unsubstituted aromatic hydrocarbon group having 6 to 20 carbon atoms, a substituted or unsubstituted aromatic heterocyclic group having 3 to 12 carbon atoms, or a linked aromatic group formed by linking 2 to 6 aromatic rings of aromatic groups each selected from the aromatic hydrocarbon group and the aromatic heterocyclic group. Ar¹ more preferably represents a substituted or unsubstituted aromatic hydrocarbon group having 6 to 10 carbon atoms, a substituted or unsubstituted aromatic heterocyclic group having 3 to 9 carbon atoms, or a linked aromatic group formed by linking 2 to 6 aromatic rings of aromatic groups each selected from a phenyl group and the aromatic heterocyclic group.

Specific examples of Ar¹ include groups each produced by removing n hydrogen atoms from benzene, naphthalene, acenaphthene, acenaphthylene, azulene, anthracene, chrysene, pyrene, perylene, phenanthrene, triphenylene, corannulene, coronene, tetracene, pentacene, fluorene, benz[a]anthracene, benzo[b]fluoranthene, benzo[a]pyrene, dibenz[a,h]anthracene, picene, tetraphenylene, anthanthrene, 1,12-benzoperylene, heptacene, hexacene, pyridine, pyrimidine, triazine, thiophene, isothiazole, triazole, pyridazine, pyrrole, pyrazole, imidazole, triazole, thiadiazole, pyrazine, furan, isoxazole, oxazole, oxadiazole, quinoline, isoquinoline, quinoxaline, quinazoline, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, or a linked aromatic compound formed by linking 2 to 6 of those compounds.

Preferred examples of Ar¹ include groups each produced by removing n hydrogen atoms from benzene, naphthalene, acenaphthene, acenaphthylene, azulene, anthracene, chrysene, pyrene, perylene, phenanthrene, triphenylene, corannulene, tetracene, fluorene, benz[a]anthracene, benzo[b]fluoranthene, benzo[a]pyrene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, or a linked aromatic compound formed by linking 2 to 6 of those compounds.

More preferred examples of $Ar^1$ include groups each produced by removing n hydrogen atoms from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, or a linked aromatic compound formed by linking 2 to 6 of those compounds.

The term linked aromatic group as used herein refers to a group obtained through the linking of the aromatic rings of a substituted or unsubstituted aromatic hydrocarbon group, or a substituted or unsubstituted aromatic heterocyclic group by direct bonding, and the aromatic rings to be linked may be identical to or different from each other. In addition, when three or more aromatic rings are linked, the linked aromatic group may be linear or branched, and a bonding (hand) may be provided from a terminal aromatic ring, or may be provided from an intermediate aromatic ring. The linked aromatic group may have a substituent. The number of carbon atoms of the linked aromatic group is the total sum of carbon atoms that the substituted or unsubstituted aromatic hydrocarbon group, or the substituted or unsubstituted aromatic heterocyclic group for forming the linked aromatic group may have.

The linked aromatic group specifically refers to a group having such a structure as represented below.

Ar1-Ar2-Ar3-Ar4  (i)

Ar5-Ar6(Ar7)-Ar8  (ii)

In the formulae, Ar1 to Ar8 each represent an aromatic hydrocarbon group or an aromatic heterocyclic group, and their respective aromatic rings are bonded to each other by direct bonding. Ar1 to Ar8 change independently of each other, and may each represent any one of an aromatic hydrocarbon group and an aromatic heterocyclic group. In addition, the linked aromatic group may be linear as represented by the formula (i), or may be branched as represented by the formula (ii). A bonding hand may be provided from Ar1 or Ar5 serving as a terminal aromatic ring, or may be provided from Ar3 or Ar6 serving an intermediate aromatic ring. The aromatic rings may each be any one of an aromatic hydrocarbon group and an aromatic heterocyclic group.

In this description, with regard to the number of carbon atoms when the range of the number of carbon atoms is defined in, for example, a substituted or unsubstituted aromatic hydrocarbon group, or a substituted or unsubstituted aromatic heterocyclic group, a substituent of any such group is excluded from the calculation of the number of carbon atoms. However, the number of carbon atoms including those of the substituent preferably falls within the range of the number of carbon atoms.

In the formula (1c), $Ar^2$ represents a monovalent group, and has at least one fluorine atom. $Ar^2$ may be identical to $Ar^1$ except the foregoing.

That is, $Ar^2$ represents a fluorine-containing aromatic group obtained by substituting an aromatic group selected from an aromatic hydrocarbon group, an aromatic heterocyclic group, and a linked aromatic group with a fluorine atom. The aromatic group is an aromatic hydrocarbon group having 6 to 30 carbon atoms, an aromatic heterocyclic group having 3 to 17 carbon atoms, or a linked aromatic group formed by linking 2 to 6 aromatic rings of aromatic groups each selected from the aromatic hydrocarbon group and the aromatic heterocyclic group. The aromatic group is preferably a substituted or unsubstituted aromatic hydrocarbon group having 6 to 20 carbon atoms, a substituted or unsubstituted aromatic heterocyclic group having 3 to 12 carbon atoms, or a linked aromatic group formed by linking 2 to 6 aromatic rings of aromatic groups each selected from the aromatic hydrocarbon group and the aromatic heterocyclic group. The aromatic group is more preferably a phenyl group or a biphenyl group.

Specific examples of the aromatic group include groups each produced by removing a hydrogen atom from benzene, naphthalene, acenaphthene, acenaphthylene, azulene, anthracene, chrysene, pyrene, perylene, phenanthrene, triphenylene, corannulene, coronene, tetracene, pentacene, fluorene, benz[a]anthracene, benzo[b]fluoranthene, benzo[a]pyrene, dibenz[a,h]anthracene, picene, tetraphenylene, anthanthrene, 1,12-benzoperylene, heptacene, hexacene, pyridine, pyrimidine, triazine, thiophene, isothiazole, triazole, pyridazine, pyrrole, pyrazole, imidazole, triazole, thiadiazole, pyrazine, furan, isoxazole, oxazole, oxadiazole, quinoline, isoquinoline, quinoxaline, quinazoline, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, or a linked aromatic compound formed by linking 2 to 6 of those compounds.

Preferred examples of the aromatic group include groups each produced by removing a hydrogen atom from benzene, naphthalene, acenaphthene, acenaphthylene, azulene, anthracene, chrysene, pyrene, perylene, phenanthrene, triphenylene, corannulene, tetracene, fluorene, benz[a]anthracene, benzo[b]fluoranthene, benzo[a]pyrene, pyridine, pyrimidine, triazine, thiophene, isothiazole, triazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, or a linked aromatic compound formed by linking 2 to 6 of those compounds. A more preferred example of the aromatic group is a group produced by removing a hydrogen atom from benzene or a linked aromatic compound formed by linking 2 benzene rings.

$Ar^2$ represents the aromatic hydrocarbon group, the aromatic heterocyclic group, or the linked aromatic group described above, and these aromatic groups each have at least one fluorine atom. Although the fluorine atom may be bonded to an aromatic ring-forming carbon atom of any such aromatic group, or may be bonded to a substituent, such as an alkyl group, with which any such aromatic group is substituted, the former case is preferred. In addition, the number of the fluorine atoms is preferably from 1 to 6, more preferably from 1 to 3.

A fluorine atom is an electron-withdrawing substituent, and the introduction of the fluorine atom reduces the HOMO level of the compound represented by the general formula (1) to increase the HOMO-LUMO gap thereof. It is assumed that as a result of the foregoing, the emission of blue light having a shorter wavelength can be obtained.

In the formula (1a) or the formula (1b), $R^1$s each independently represent an aliphatic hydrocarbon group having 1 to 10 carbon atoms, a substituted or unsubstituted diarylamino group having 12 to 44 carbon atoms, a substituted or unsubstituted aromatic hydrocarbon group having 6 to 18 carbon atoms, or a substituted or unsubstituted aromatic heterocyclic group having 3 to 17 carbon atoms. It is preferred that $R^1$s each independently represent an aliphatic hydrocarbon group having 1 to 8 carbon atoms, a substituted or unsubstituted diarylamino group having 12 to 22 carbon atoms, a substituted or unsubstituted aromatic hydrocarbon group having 6 to 12 carbon atoms, or a substituted or unsubstituted aromatic heterocyclic group having 3 to 15 carbon atoms. It is more preferred that $R^1$s each independently represent a substituted or unsubstituted aromatic hydrocarbon group having 6 to 10 carbon atoms, or a substituted or unsubstituted aromatic heterocyclic group having 3 to 10 carbon atoms.

a represents an integer of from 0 to 4, preferably represents an integer of from 0 to 2, and more preferably represents an integer of 0 or 1. b represents an integer of from 0 to 2, and preferably represents an integer of 0 or 1.

Specific examples of the $R^1$ include alkyl groups, such as methyl, ethyl, propyl, butyl, pentyl, hexyl, heptyl, octyl, nonyl, and decyl, diphenylamino, naphthylphenylamino, dinaphthylamino, dianthranylamino, diphenanthrenylamino, phenyl, naphthyl, pyridyl, pyrimidyl, triazyl, dibenzofuranyl, dibenzothienyl, and carbazolyl.

Preferred examples of the $R^1$ include methyl, ethyl, propyl, butyl, pentyl, hexyl, heptyl, octyl, diphenylamino, naphthylphenylamino, dinaphthylamino, phenyl, naphthyl, pyridyl, pyrimidyl, triazyl, dibenzofuranyl, dibenzothienyl, and carbazolyl. More preferred examples of the $R^1$ include phenyl, naphthyl, pyridyl, pyrimidyl, and triazyl.

Preferred modes of the general formula (1) are the general formulae (3) to (8). In each of the general formulae (3) to (8), $Ar^2$, a, b, and $R^1$ are identical in meaning to those of the general formula (1). The total number of carbon atoms of L-$Ar^3$ does not exceed the number of carbon atoms of $Ar^1$ because L-$Ar^3$ corresponds to $Ar^1$ when $Ar^1$ of the general formula (1) represents a monovalent group.

L represents a single bond or a divalent group. When L represents a divalent group, the divalent group is a substituted or unsubstituted aromatic hydrocarbon group having 6 to 12 carbon atoms, or a substituted or unsubstituted aromatic heterocyclic group having 3 to 10 carbon atoms. L preferably represents a single bond, a substituted or unsubstituted aromatic hydrocarbon group having 6 to 10 carbon atoms, or a substituted or unsubstituted aromatic heterocyclic group having 3 to 8 carbon atoms, and more preferably represents a single bond, a substituted or unsubstituted phenyl group, or a substituted or unsubstituted aromatic heterocyclic group having 3 to 6 carbon atoms.

Specific examples of the L include a single bond, and a group produced by removing 2 hydrogen atoms from benzene, naphthalene, acenaphthene, acenaphthylene, azulene, pyridine, pyrimidine, triazine, thiophene, isothiazole, triazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, or the like.

Preferred examples of the L include a single bond, and a group produced from benzene, naphthalene, pyridine, pyrimidine, triazine, thiophene, isothiazole, triazole, pyridazine, pyrrole, pyrazole, imidazole, triazole, thiadiazole, pyrazine, furan, isoxazole, oxazole, oxadiazole, quinoxaline, quinazoline, oxadiazole, thiadiazole, benzotriazine, phthalazine, tetrazole, indole, benzofuran, benzothiophene, benzoxazole, benzothiazole, indazole, benzimidazole, or the like. More preferred examples of the L include a single bond, and a group produced from benzene, pyridine, pyrimidine, triazine, or thiophene.

In each of the general formulae (3) to (8), $Ar^3$ represents a heterocyclic group represented by the formula (3b).

In the formula (3b), Xs each represent $CR^2$ or N, and at least one of Xs represents N. $R^2$ represents hydrogen, an aliphatic hydrocarbon group having 1 to 10 carbon atoms, a substituted or unsubstituted aromatic hydrocarbon group having 6 to 18 carbon atoms, a substituted or unsubstituted aromatic heterocyclic group having 3 to 10 carbon atoms, or a linked aromatic group formed by linking 2 to 4 aromatic rings of aromatic groups each selected from the aromatic hydrocarbon group and the aromatic heterocyclic group. $R^2$ preferably represents hydrogen, a substituted or unsubstituted aromatic hydrocarbon group having 6 to 12 carbon atoms, a substituted or unsubstituted aromatic heterocyclic group having 3 to 8 carbon atoms, or a linked aromatic group formed by linking 2 to 4 aromatic rings of aromatic groups each selected from the aromatic hydrocarbon group and the aromatic heterocyclic group. $R^2$ more preferably represents hydrogen, a substituted or unsubstituted phenyl group, a substituted or unsubstituted aromatic heterocyclic group having 3 to 6 carbon atoms, or a linked aromatic group formed by linking 2 or 3 aromatic rings of aromatic groups each selected from the phenyl group and the aromatic heterocyclic group. The description of the linked aromatic group is identical to the foregoing.

In this description, when an aromatic hydrocarbon group, an aromatic heterocyclic group, or the like has a substituent, examples of the substituent include a cyano group, an aliphatic hydrocarbon group having 1 to 10 carbon atoms, an alkoxy group having 1 to 10 carbon atoms, an alkylthio group having 1 to 10 carbon atoms, and an alkylsilyl group having 3 to 30 carbon atoms. Preferred examples thereof include a cyano group, an aliphatic hydrocarbon group having 1 to 8 carbon atoms, an alkoxy group having 1 to 8 carbon atoms, an alkylthio group having 1 to 8 carbon atoms, and an alkylsilyl group having 3 to 20 carbon atoms. More preferred examples thereof include an aliphatic hydrocarbon group having 1 to 6 carbon atoms, an alkoxy group having 1 to 6 carbon atoms, an alkylthio group having 1 to 6 carbon atoms, and an alkylsilyl group having 3 to 10 carbon atoms.

Specific examples of the compound represented by the general formula (1) are shown below. However, the compound is not limited to these exemplified compounds.

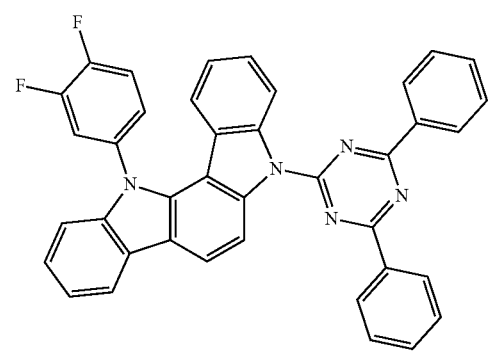
101
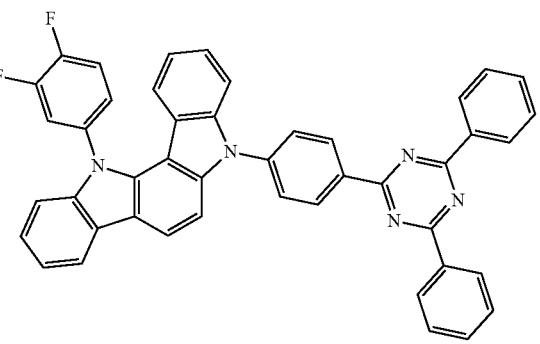
104
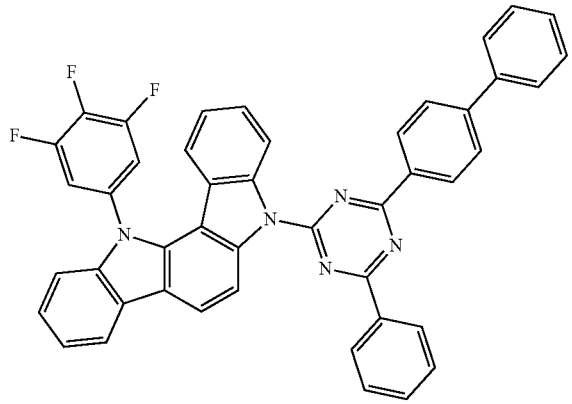
102
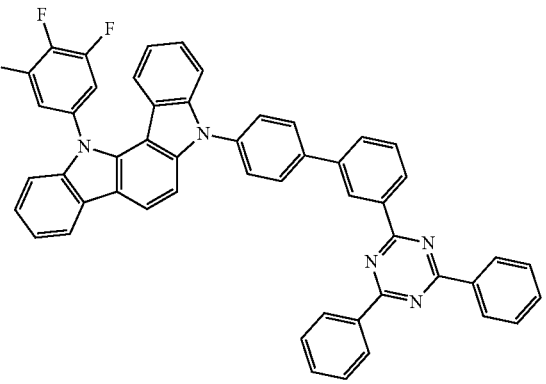
105
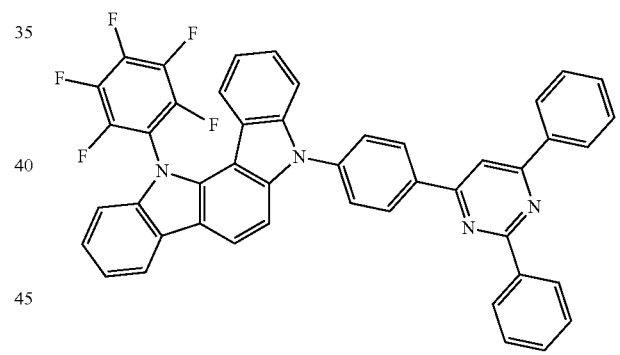
106
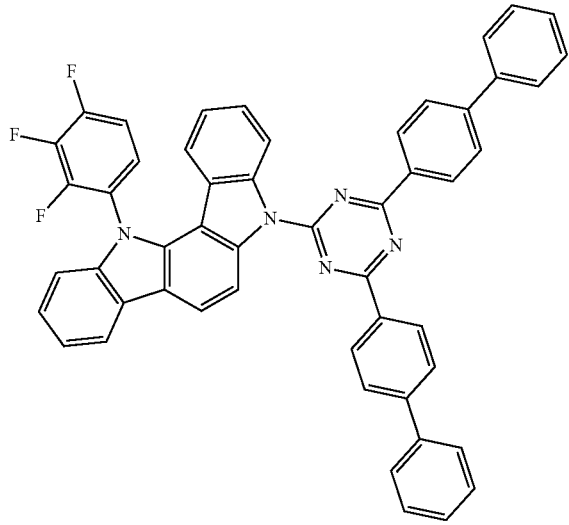
103
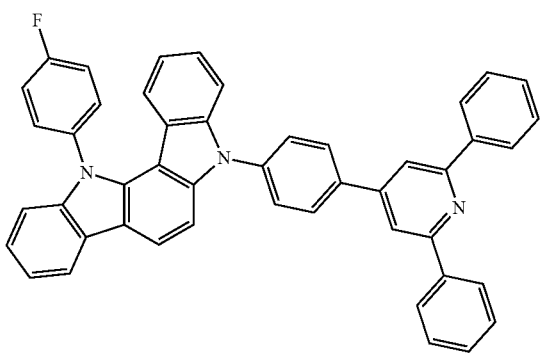
107

-continued
108
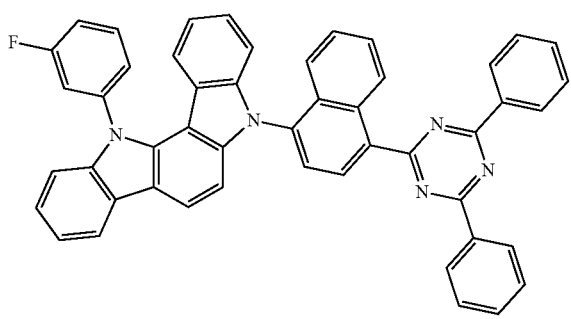
109
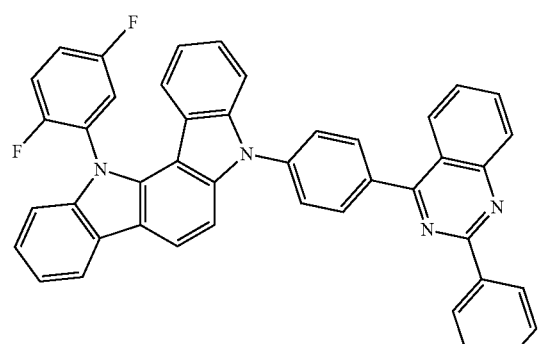
110
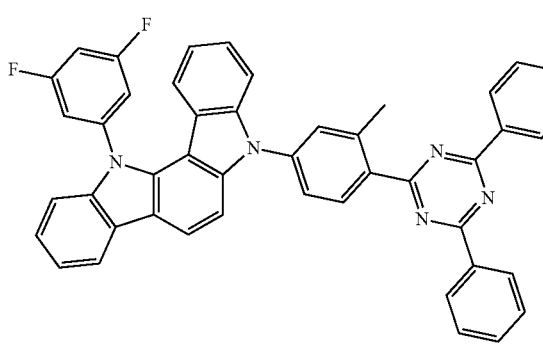
111
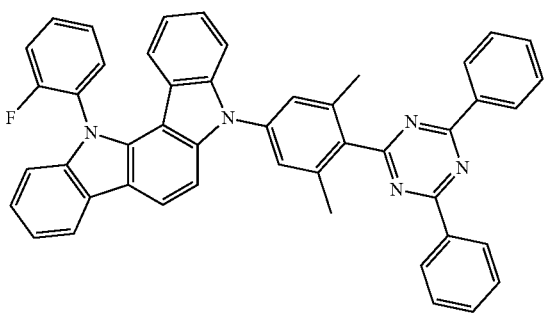
-continued
112
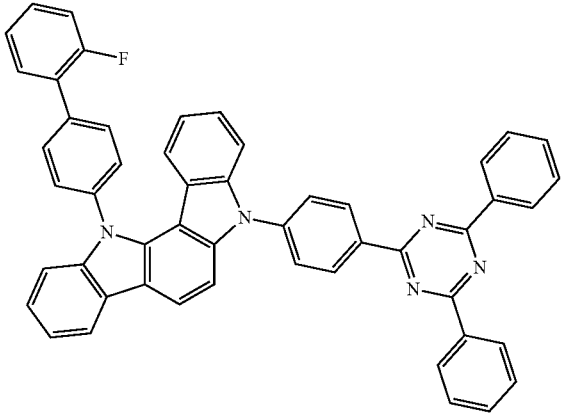
113
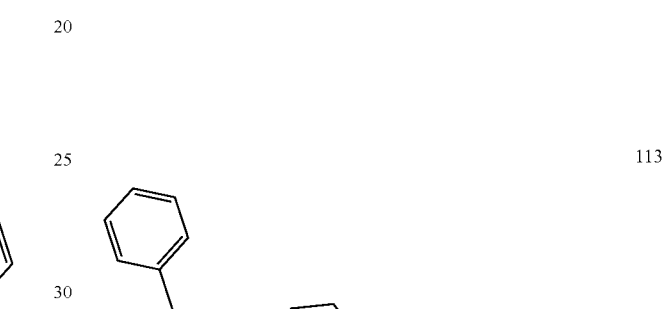
114
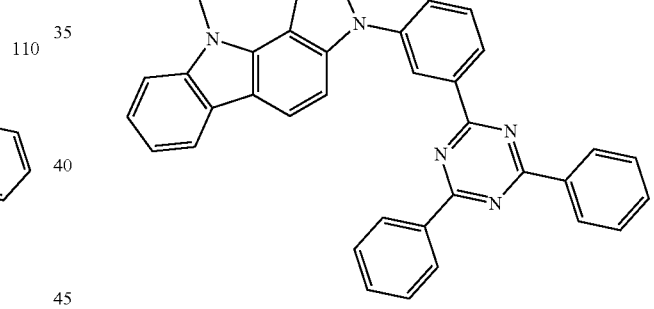

115
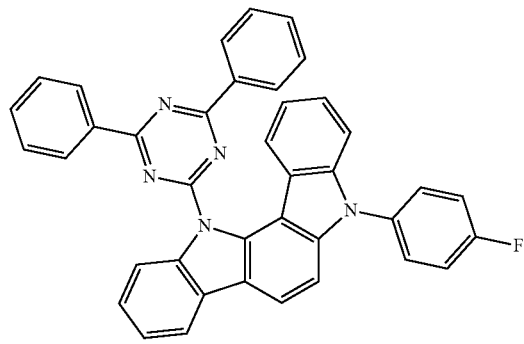
116
118
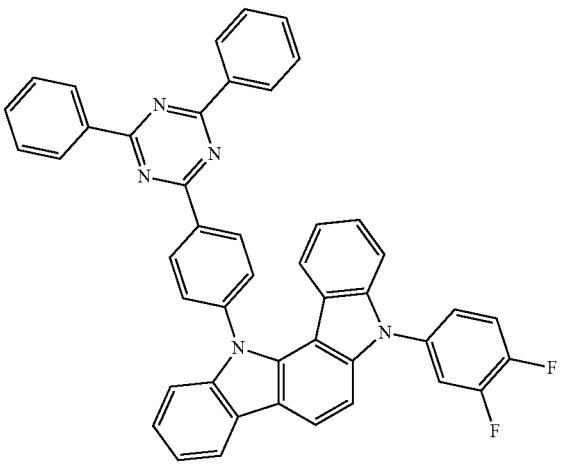
119
117
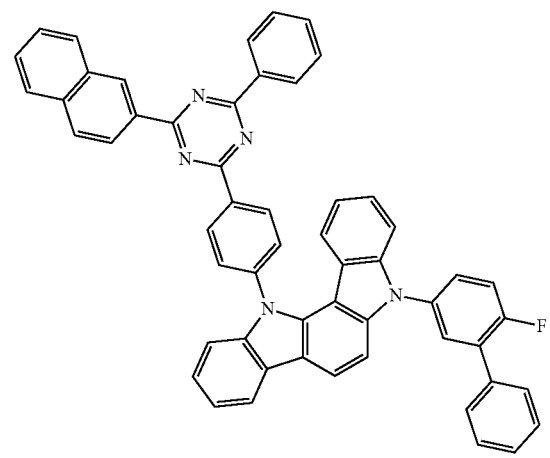
120
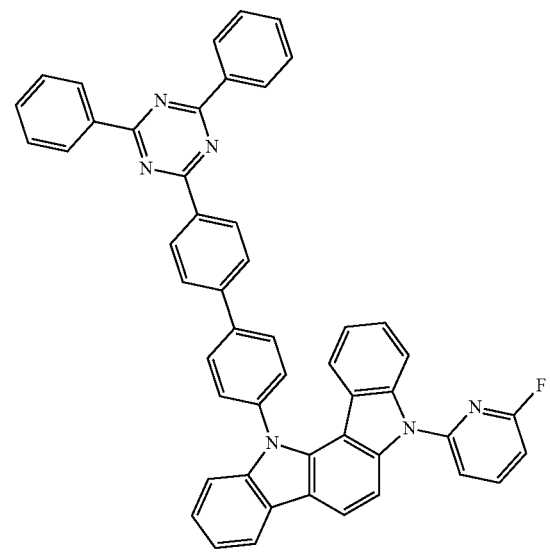

-continued
121
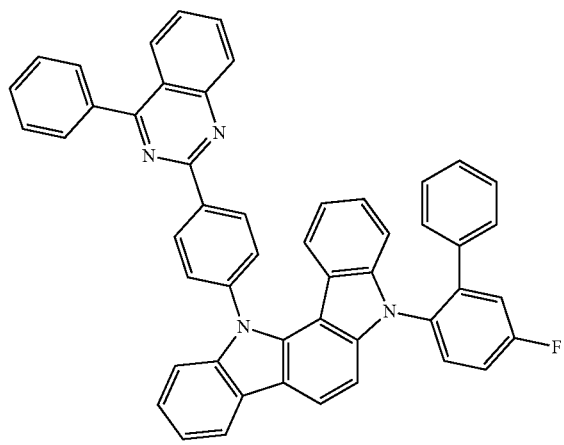
122
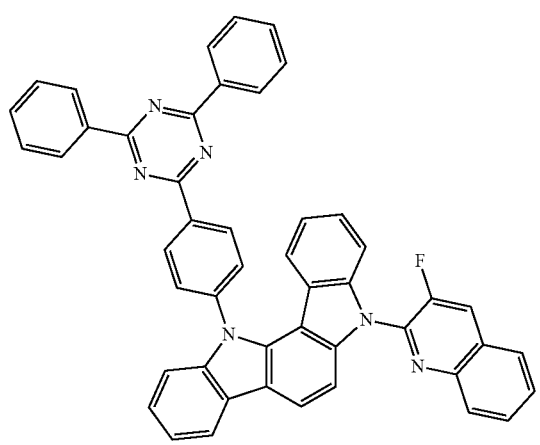
123
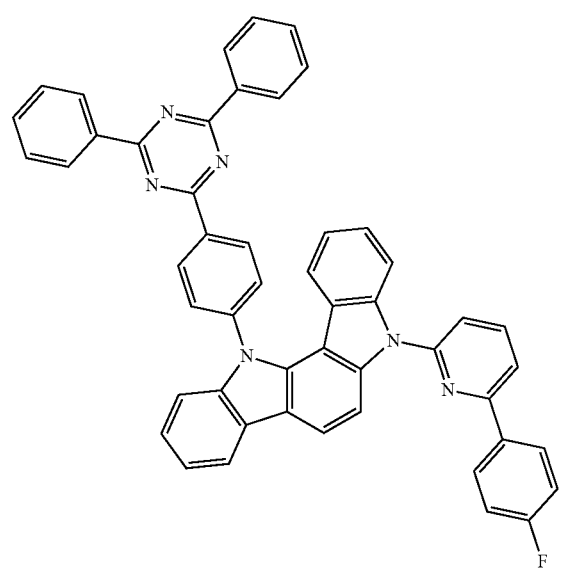
124
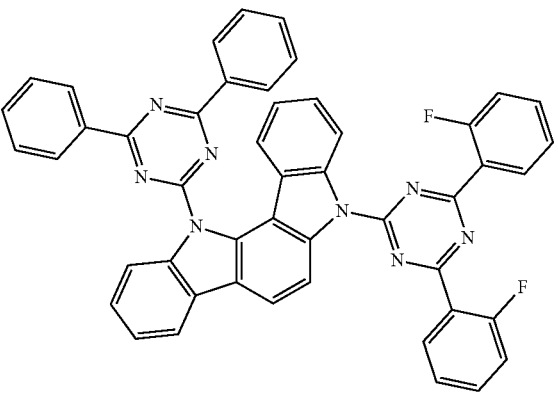
125
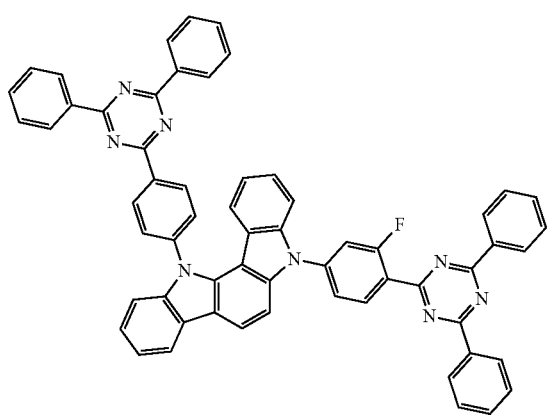
126
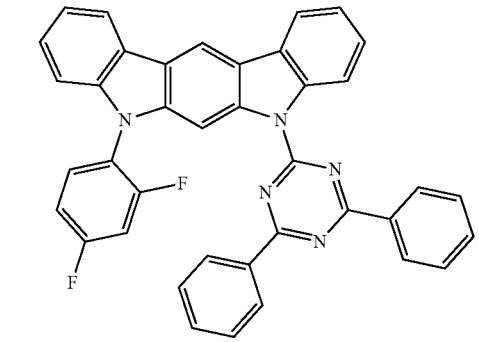
127

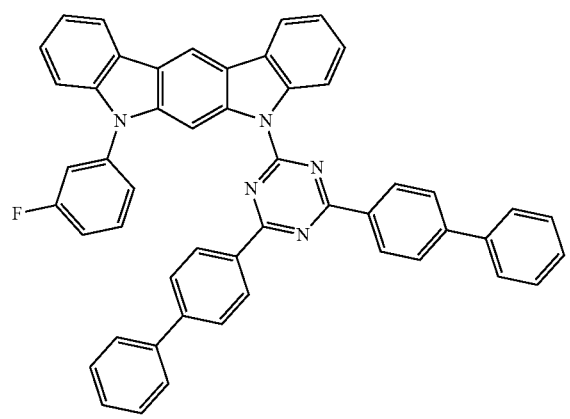
128
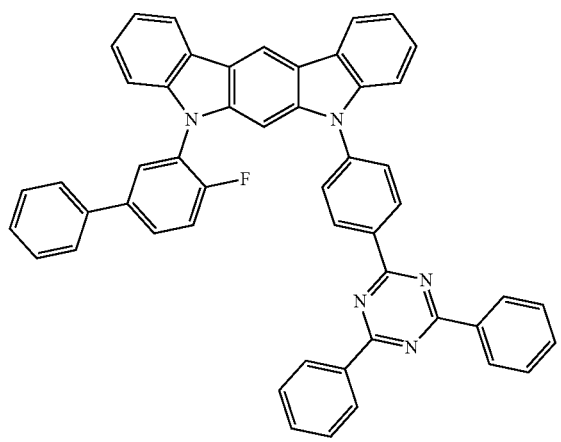
131
129
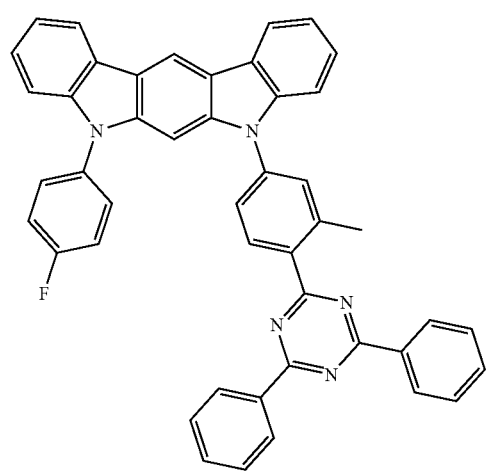
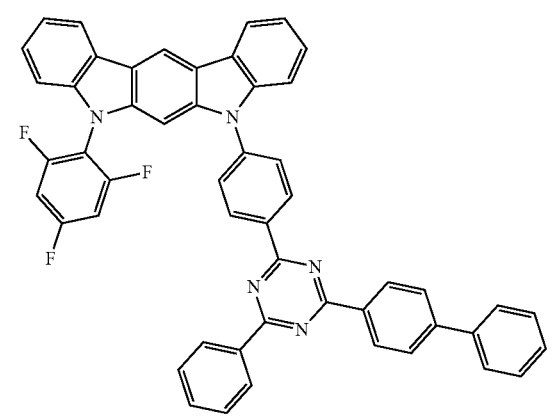
132
130
133

134
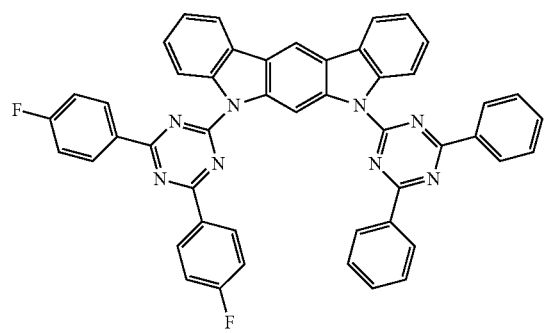
135
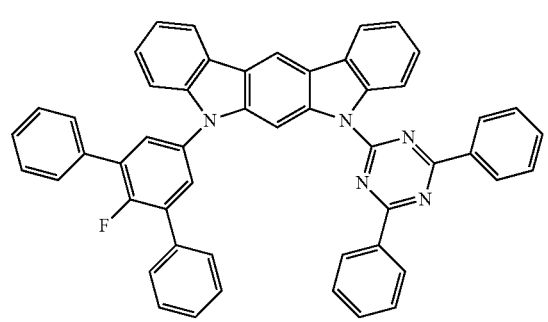
136
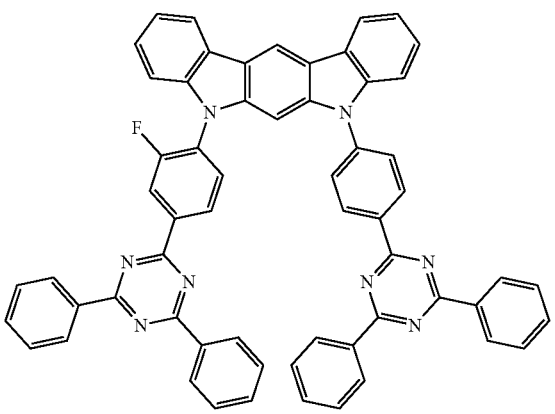
137
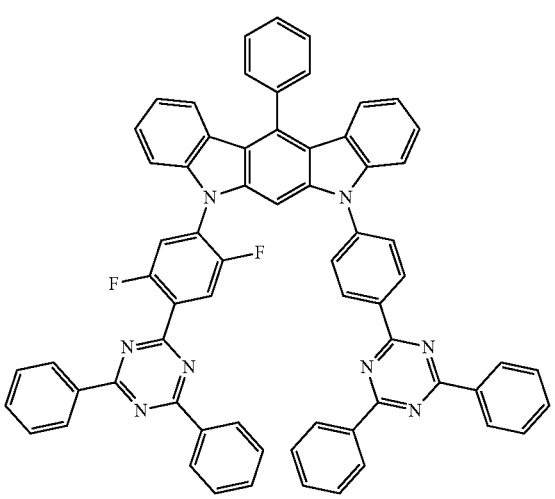
138
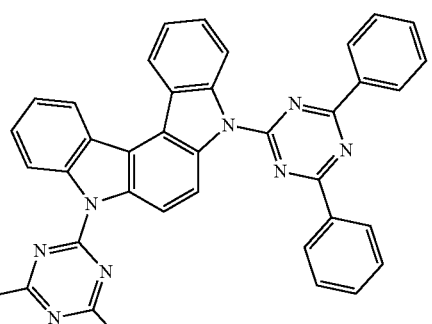
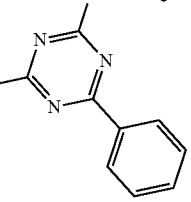
139
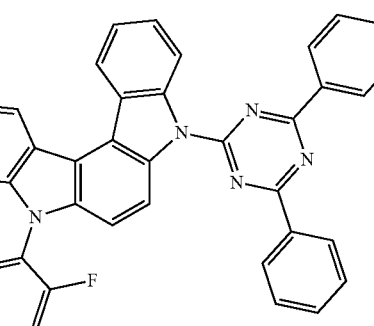
140
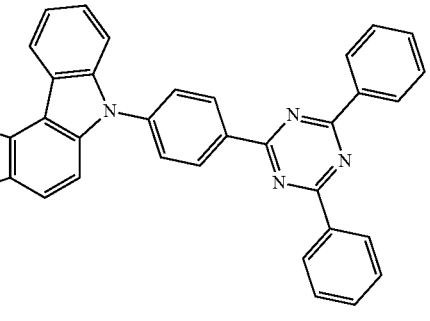
141
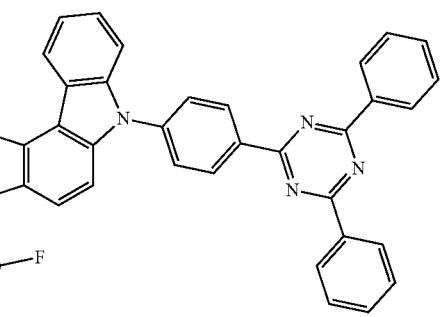

142
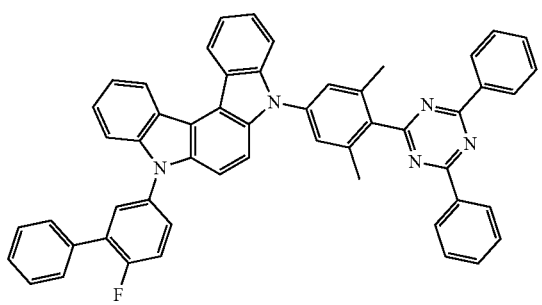
143
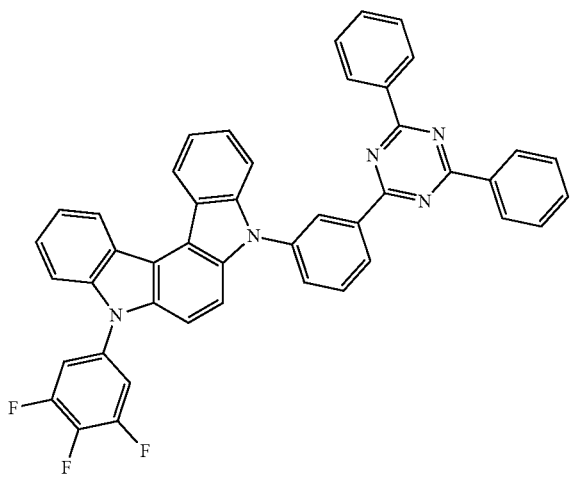
144
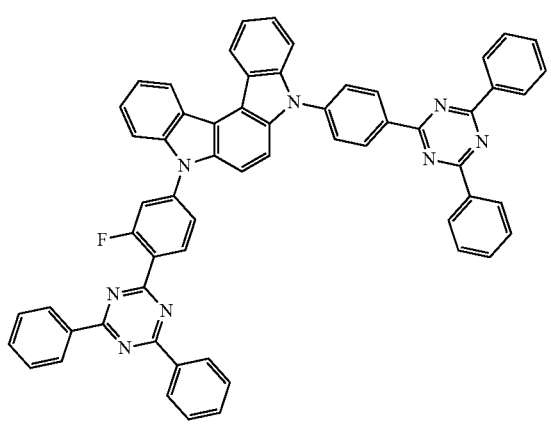
145
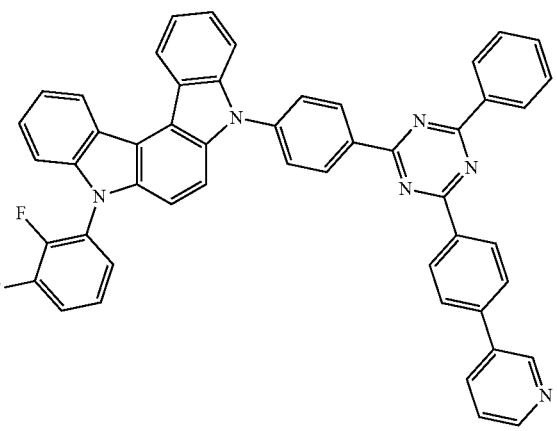
146
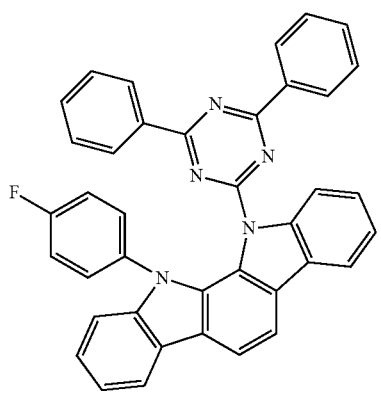
147
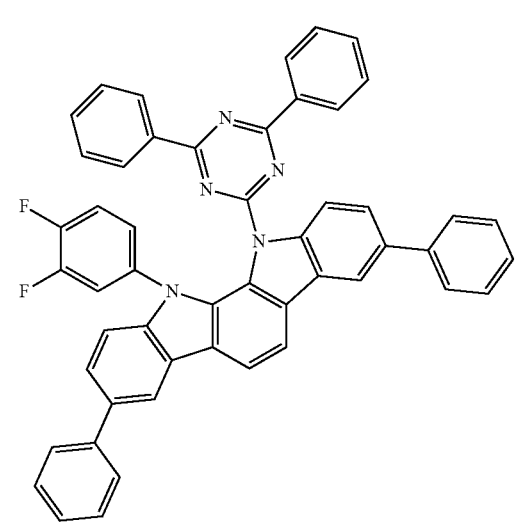

148
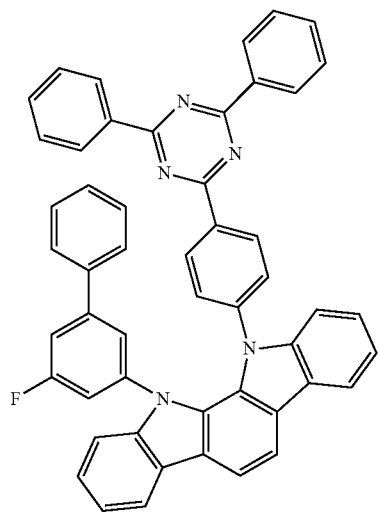
149
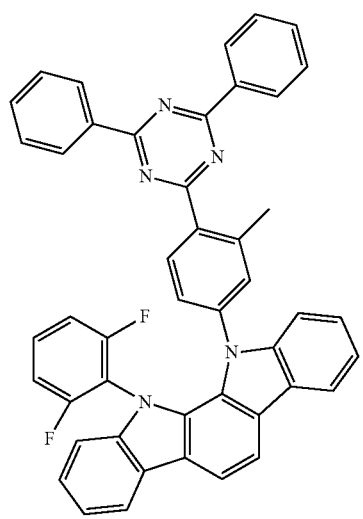
150
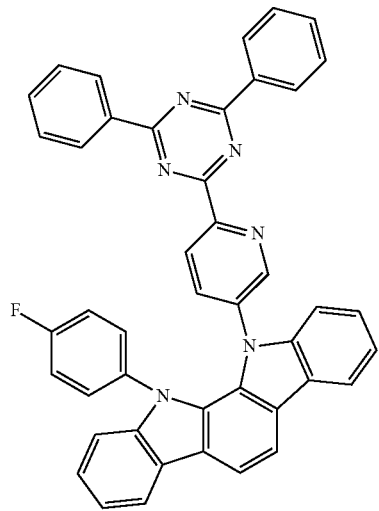
151
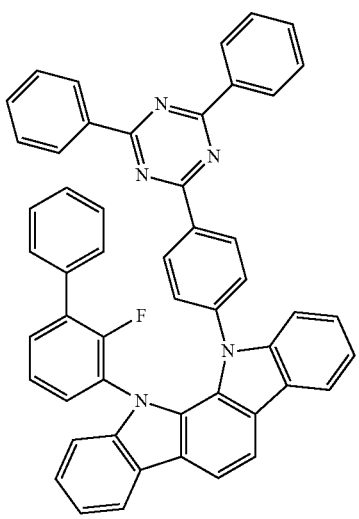
152
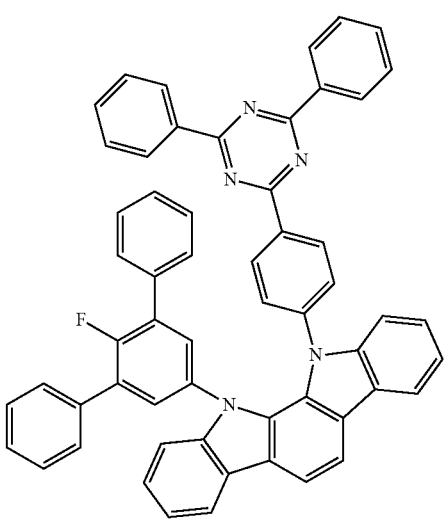
153
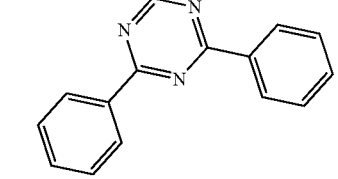

154
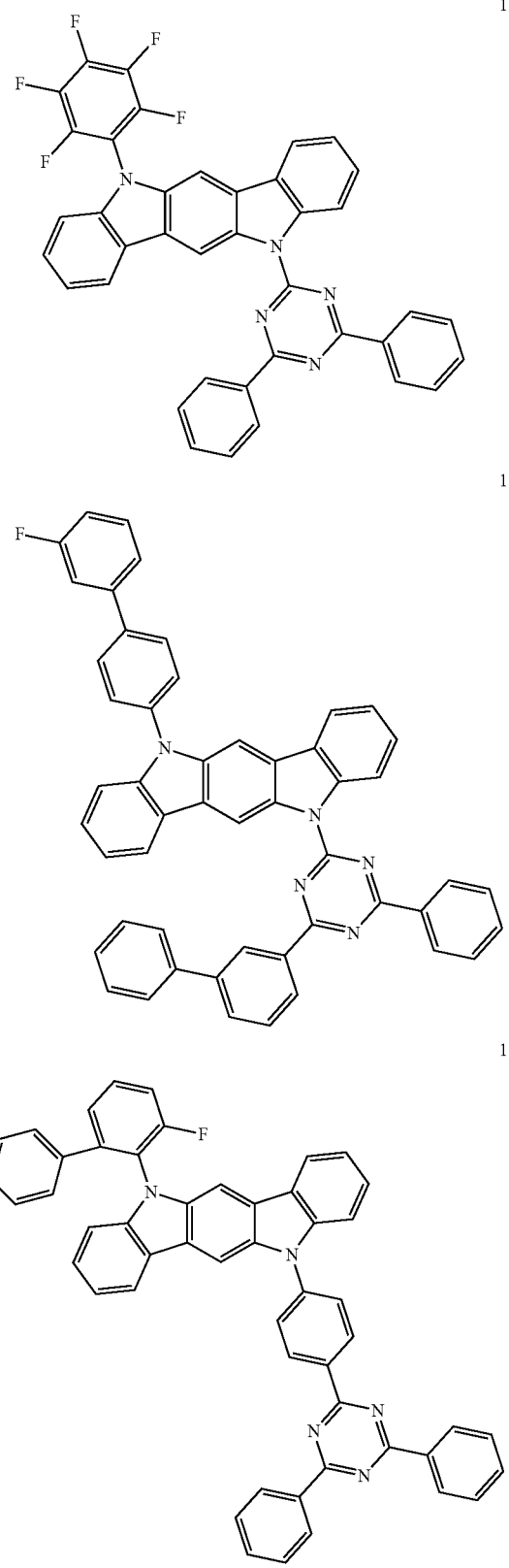
155
156
157
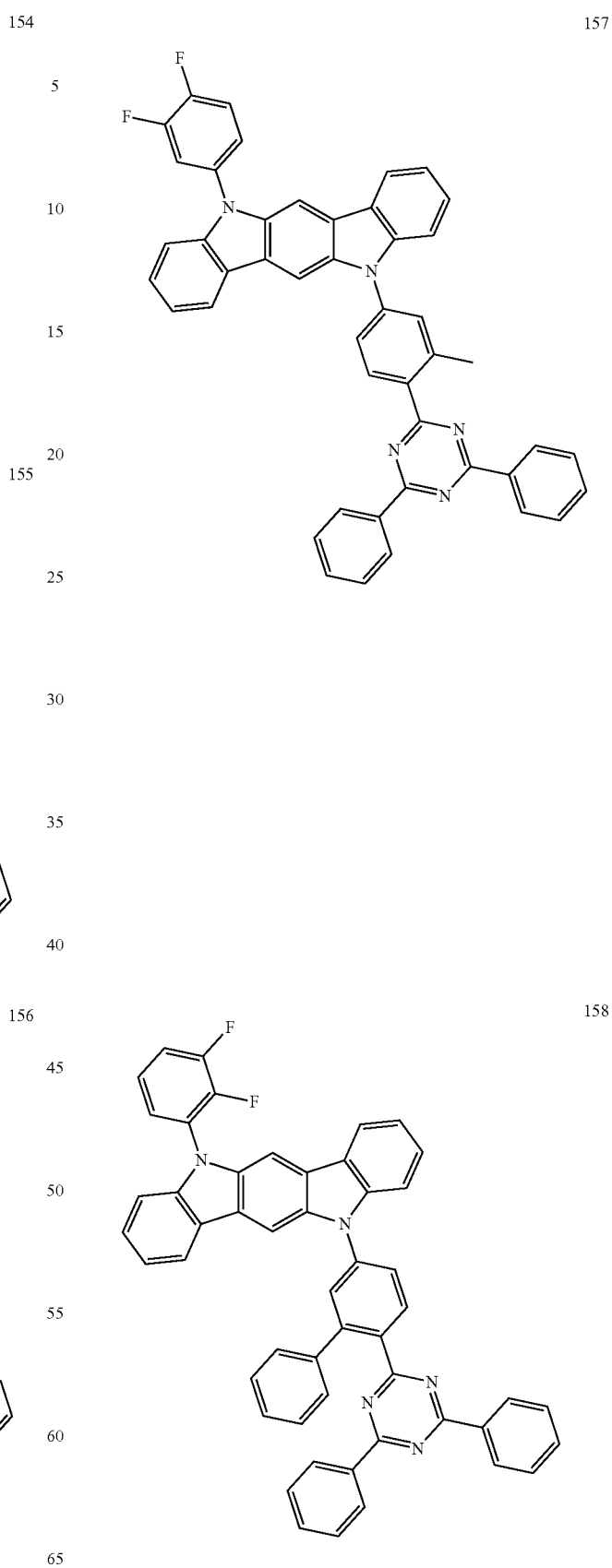
158

159
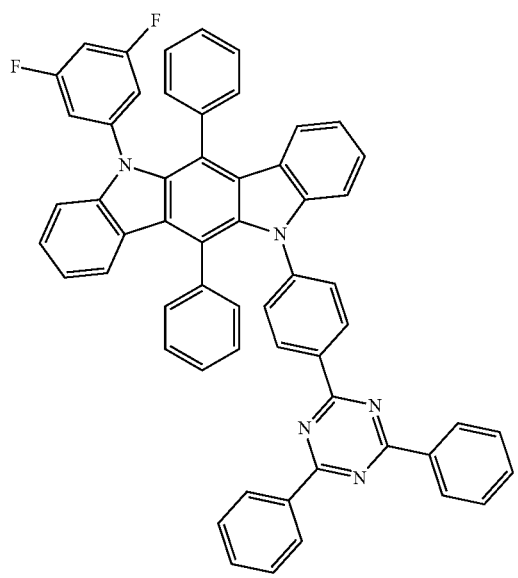
160
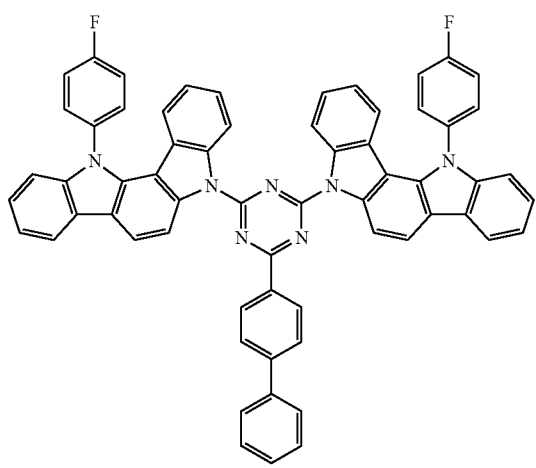
161
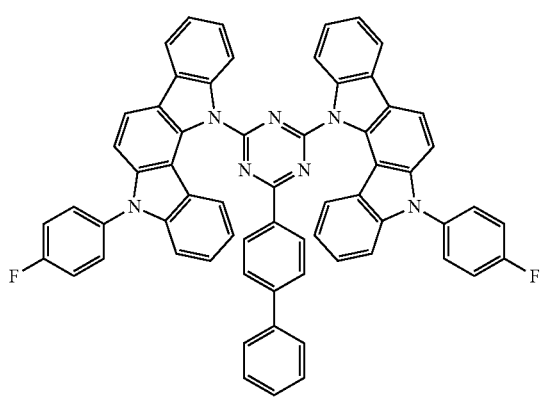
162
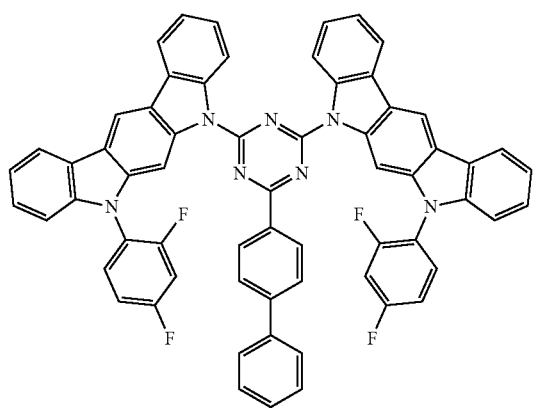
163
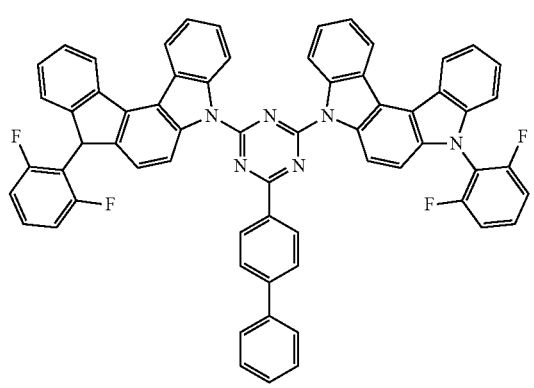
164
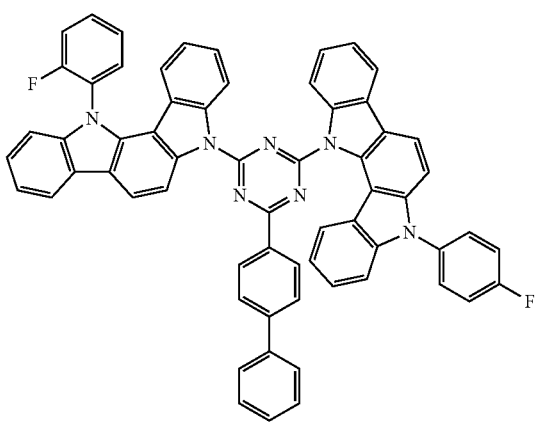

165

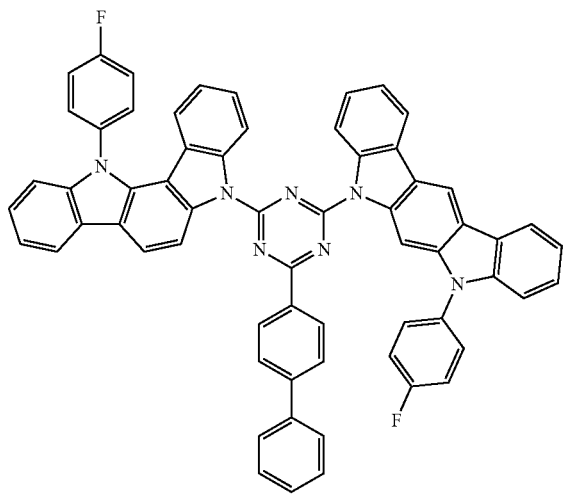

166

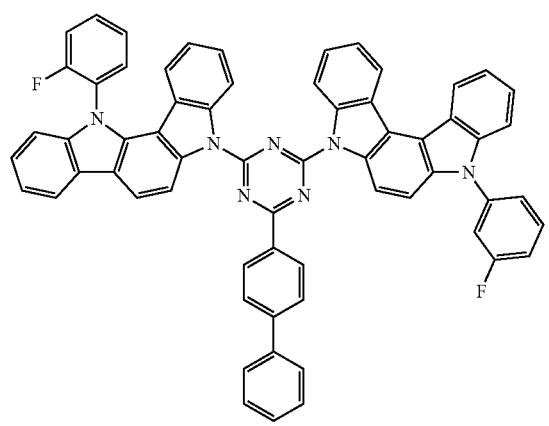

167

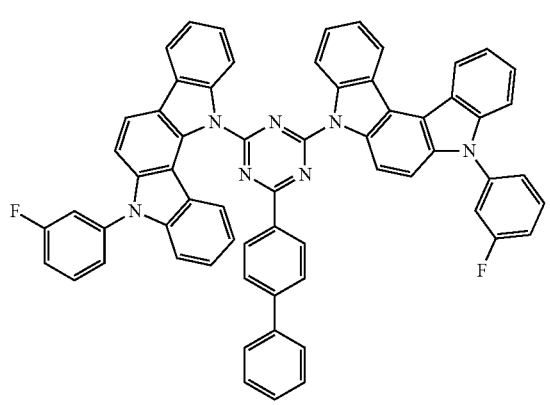

168

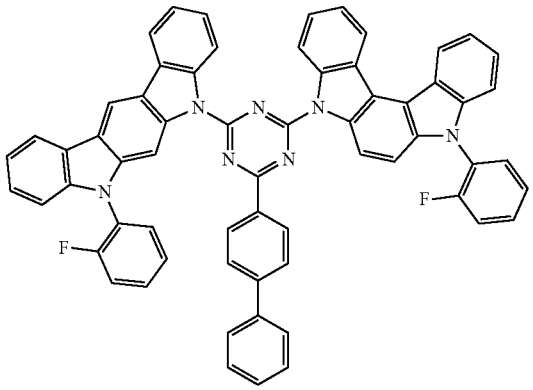

169

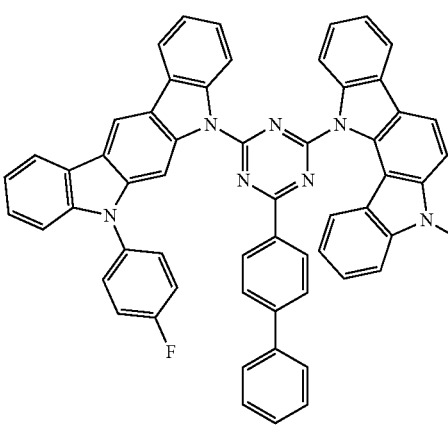

170

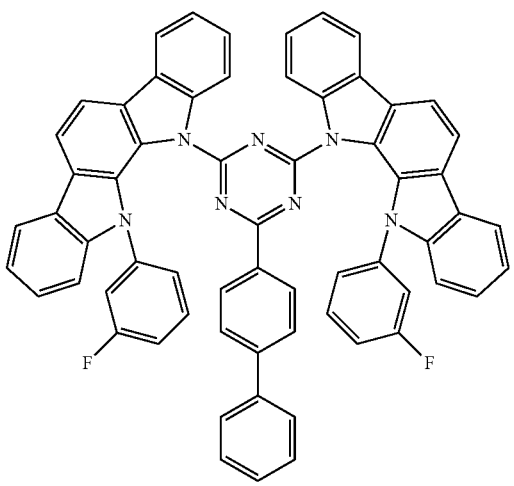

The thermally activated delayed fluorescent light-emitting material to be used in the organic EL device of the present invention is a compound represented by the general formula (1), and has a thermally activated delayed fluorescent light-emitting property.

It has been known that a difference (ΔE) between the excited singlet energy (S1) and excited triplet energy (T1) of a material having a thermally activated delayed fluorescent light-emitting property is small.

The difference (ΔE) between the excited singlet energy (S1) and excited triplet energy (T1) of the compound represented by the general formula (1) is preferably 0.2 eV or less. When the compound shows such ΔE, the compound serves as an excellent TADF material.

The presence or absence of thermally activated delayed fluorescent light emission may be judged by a method described in Examples.

An excellent delayed fluorescent organic EL device may be obtained by incorporating the compound represented by the general formula (1) as a TADF material into a light-emitting layer.

In addition, a host material may be incorporated into the light-emitting layer together with the TADF material as required. The incorporation of the host material provides an excellent organic EL device. In this case, the TADF material is also referred to as dopant. The host material accelerates the emission of light from the TADF material that is a dopant. The host material desirably has an excited triplet energy (T1) larger than the excited singlet energy (S1) of the TADF material.

A carbazole compound represented by the general formula (9) is suitable as the host material.

In the general formula (9), $Ar^4$ represents a p-valent group, and represents a group produced by removing p hydrogen atoms from benzene, a nitrogen-containing six-membered heterocyclic compound, dibenzofuran, dibenzothiophene, carbazole, carborane, triazine, or a linked compound obtained by linking 2 to 4 of those compounds. In this case, the linked compound refers to a compound having a structure obtained by linking rings of benzene, a nitrogen-containing six-membered heterocycle, dibenzofuran, dibenzothiophene, carbazole, or carborane, via direct bonding, and a group produced by removing 2 hydrogen atoms from any one of those compounds is represented by, for example, —Ar—Ar—, —Ar—Ar—Ar—, or —Ar—Ar(Ar)—. In each of those formulae, Ar represents a ring of benzene, a nitrogen-containing six-membered heterocycle, dibenzofuran, dibenzothiophene, carbazole, or carborane, and a plurality of Ars may be identical to or different from each other. A preferred example of the linked compound is biphenyl or terphenyl, which is a compound obtained by linking 2 or 3 benzene rings.

$Ar^4$ preferably represents a p-valent group produced from benzene, biphenyl, terphenyl, dibenzofuran, N-phenylcarbazole, carborane, triazine, or a linked compound obtained by linking 2 or 3 of those compounds. p represents an integer of 1 or 2, preferably an integer of 1. q represents an integer of from 0 to 4, preferably an integer of from 0 to 3, more preferably an integer of from 0 to 2, and when $Ar^4$ represents a p-valent group produced from benzene, q does not represent 0.

The carbazole compound has $Ar^4$ and a carbazole ring, and the $Ar^4$ and the carbazole ring may each have a substituent as long as the function of the compound as a host is not inhibited. Examples of such substituent include a hydrocarbon group having 1 to 8 carbon atoms and an alkoxy group having 1 to 8 carbon atoms. Of those, an alkyl group having 1 to 3 carbon atoms or an alkoxy group having 1 to 3 carbon atoms is preferred.

Specific examples of the carbazole compound represented by the general formula (9) are shown below.

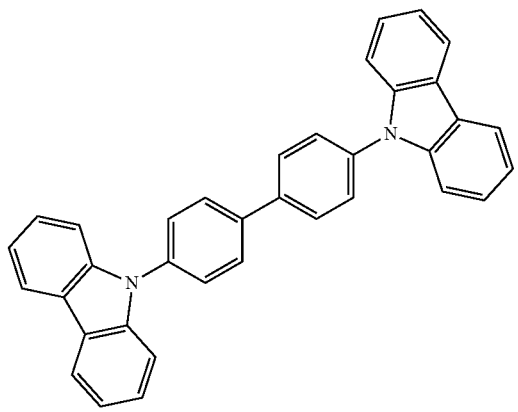

201

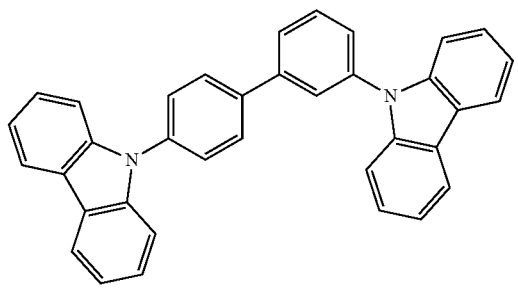

202

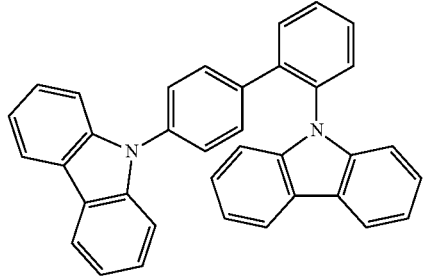

203

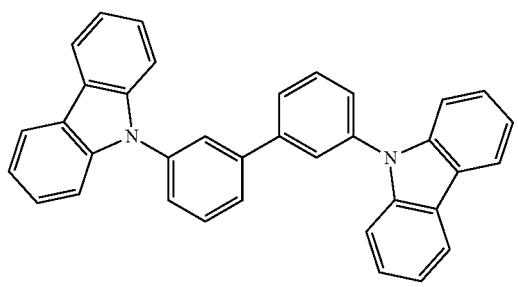

204

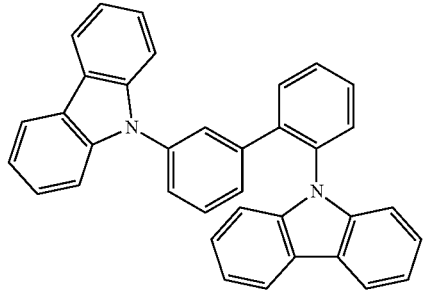

205

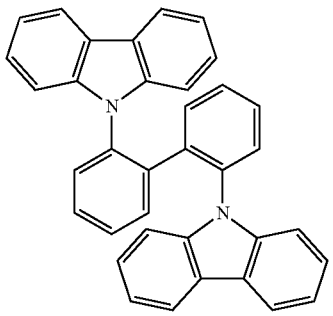
206
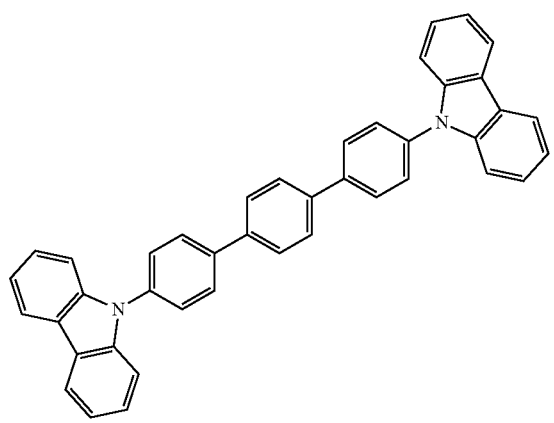
207
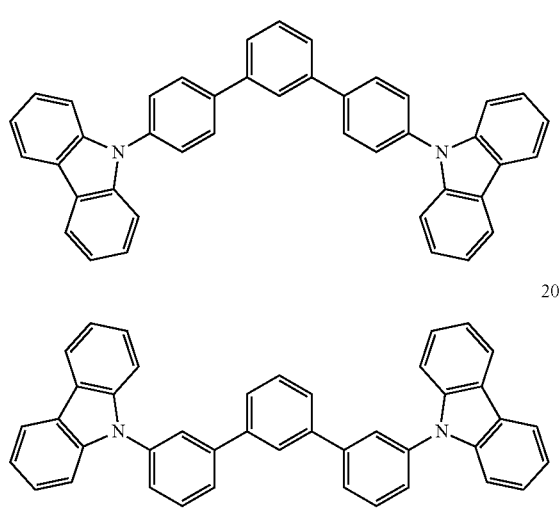
208
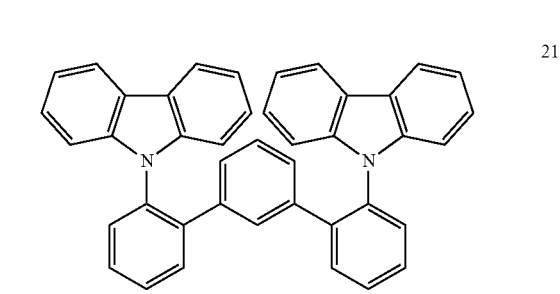
209
210
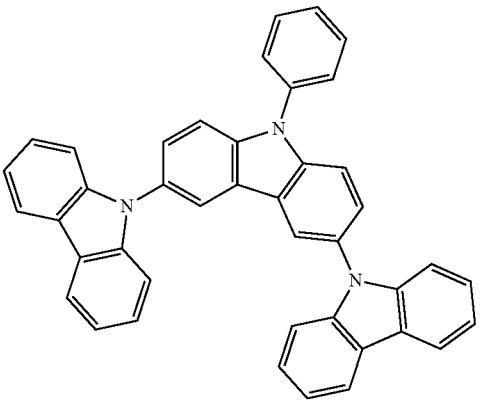
211
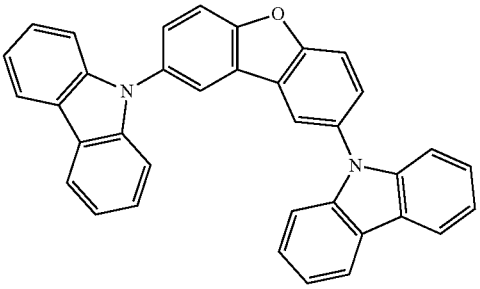
212
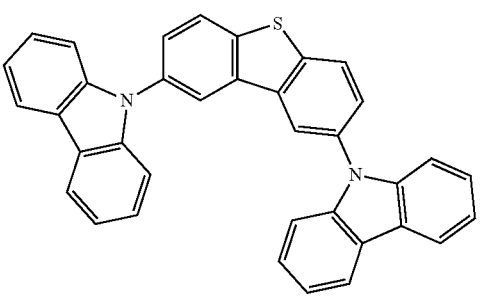
213
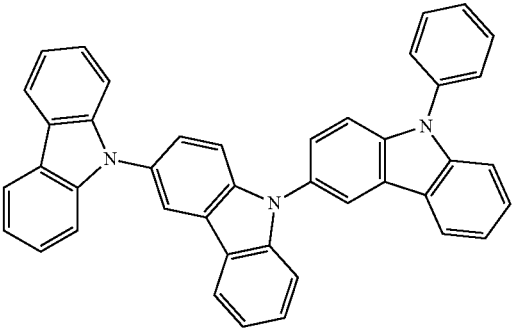
214

215
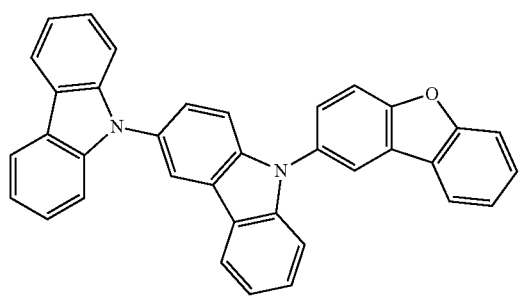
216
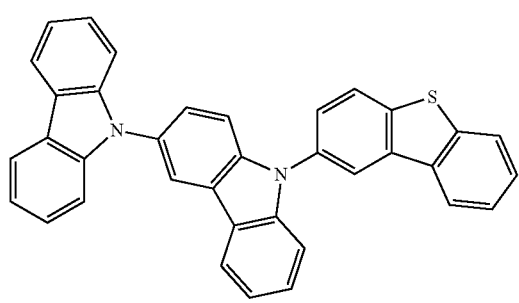
217
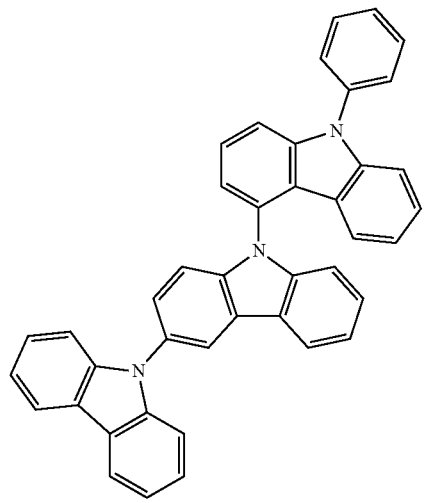
218
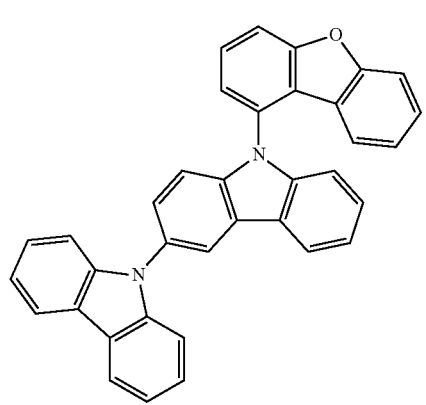
219
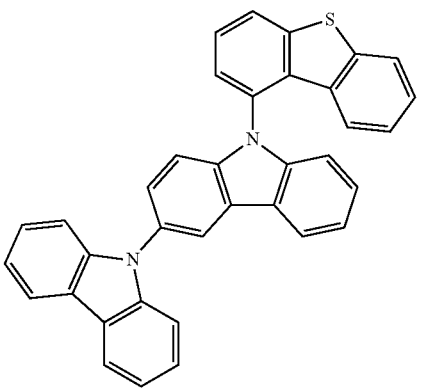
220
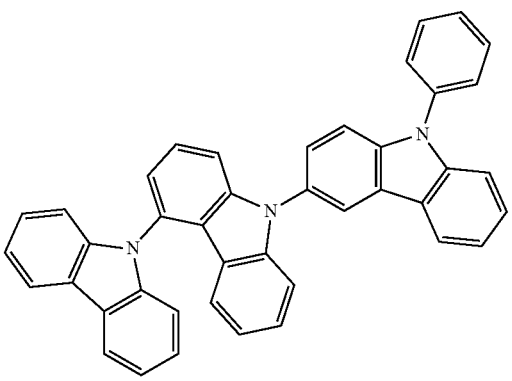
221
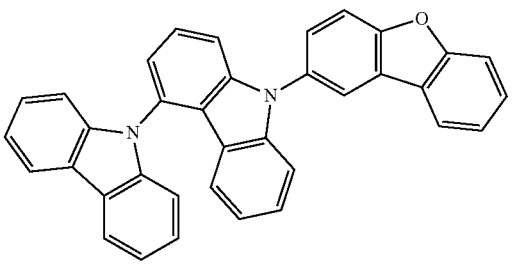
222
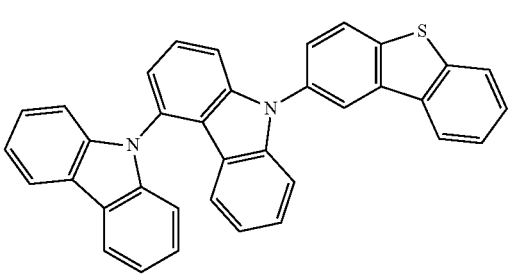

223
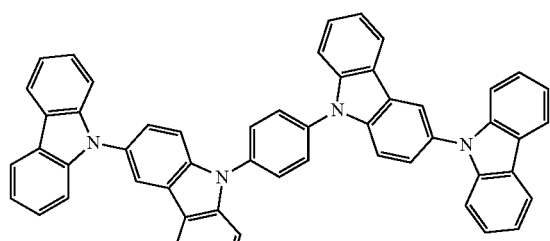
224
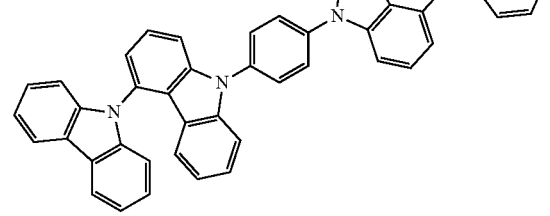
225
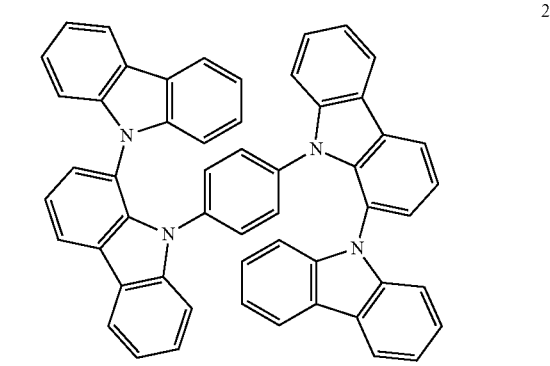
226
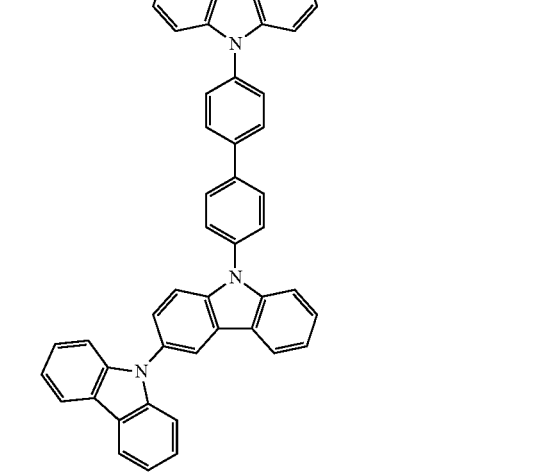
227
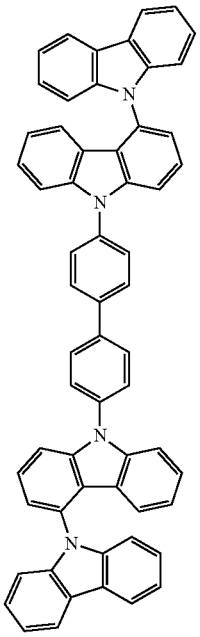
228
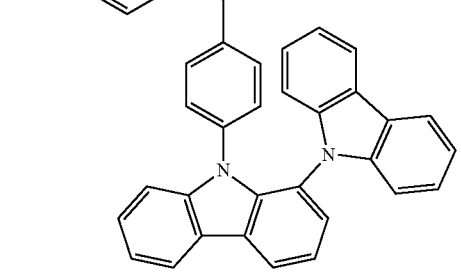
229
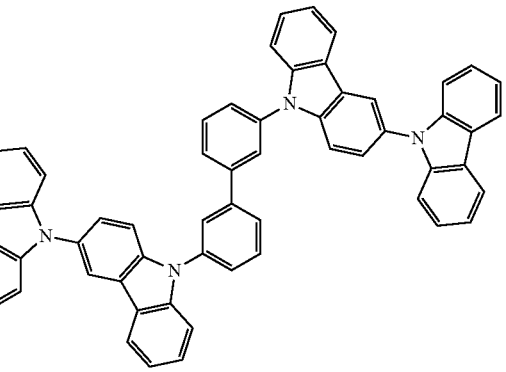

230
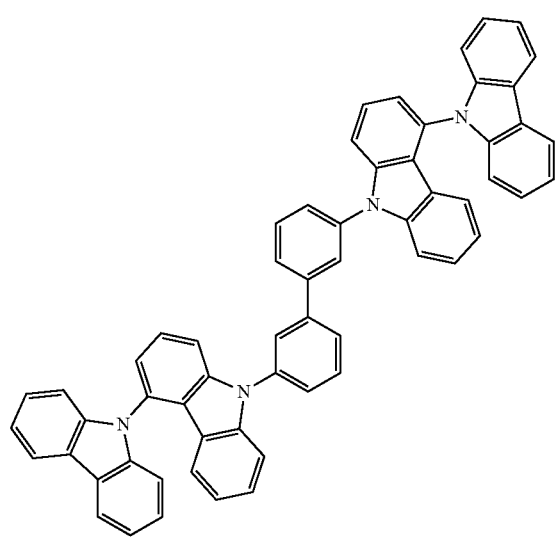
231
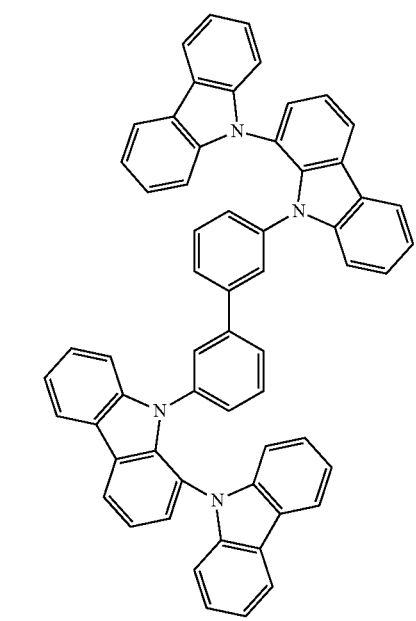
232
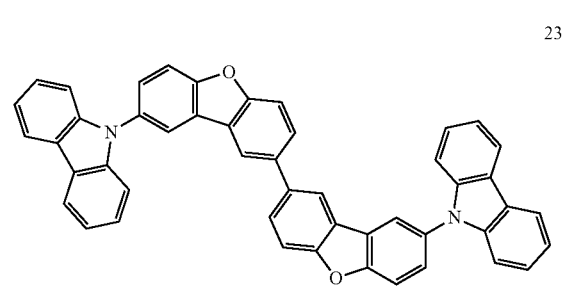
233
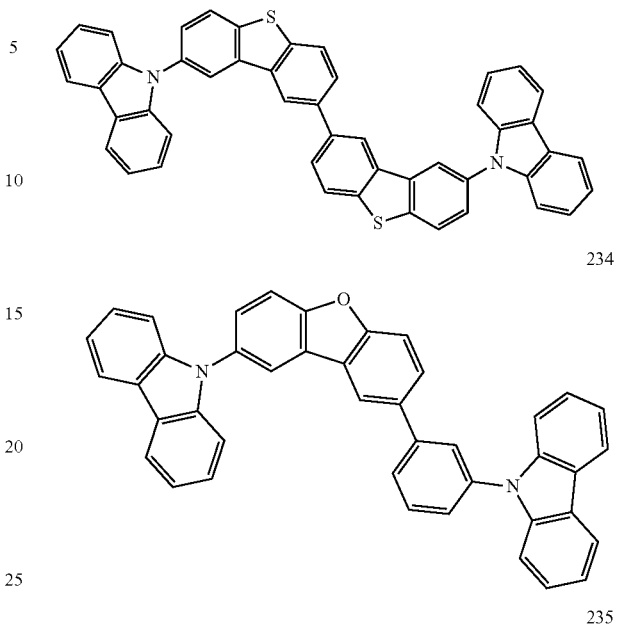
234
235
236
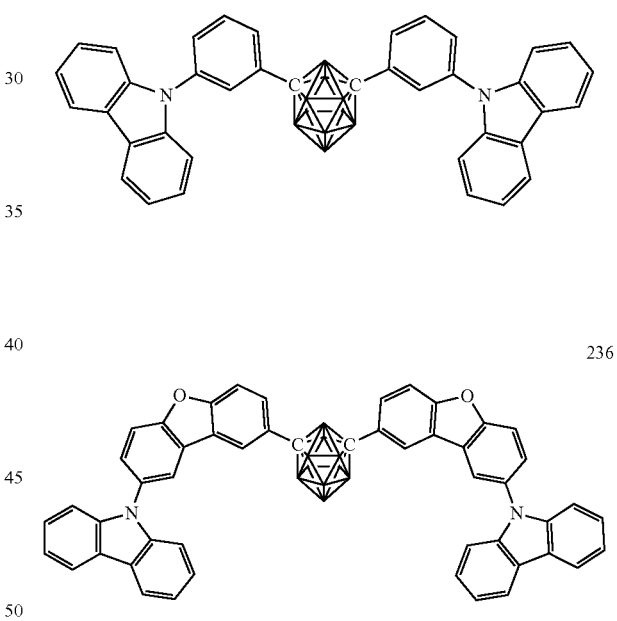
237
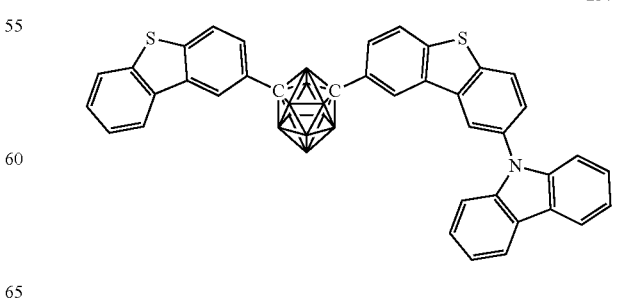

238
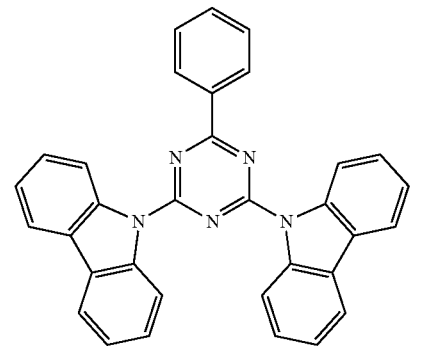
239
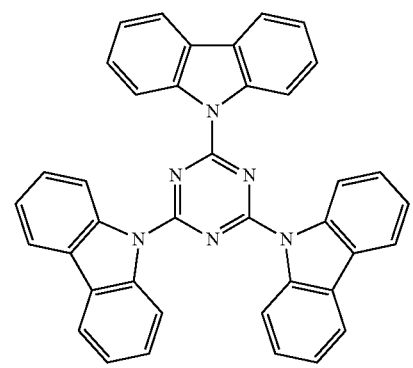
240
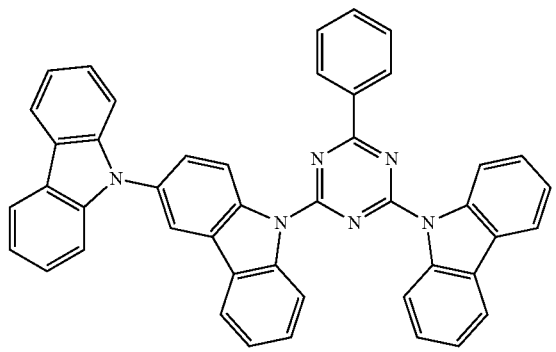
241
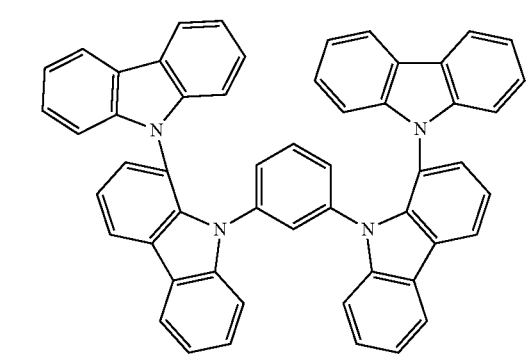
242
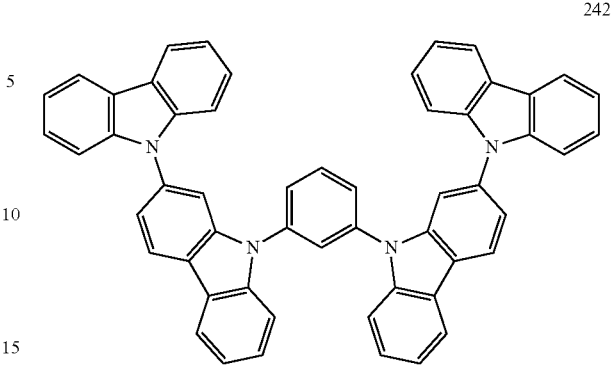
243
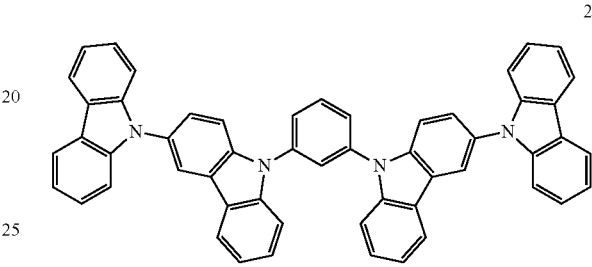
244
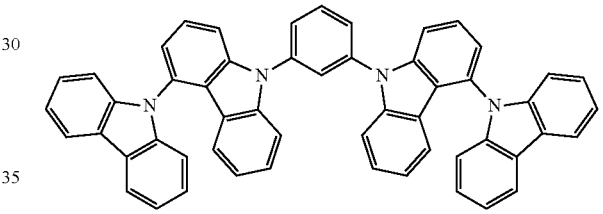
245
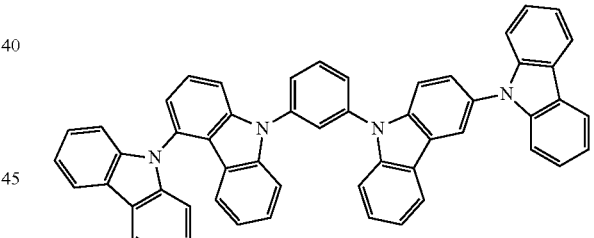
246
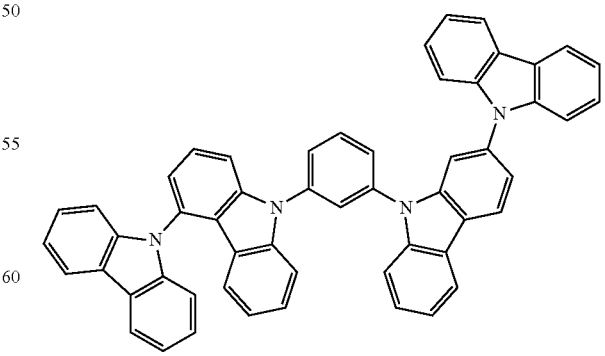

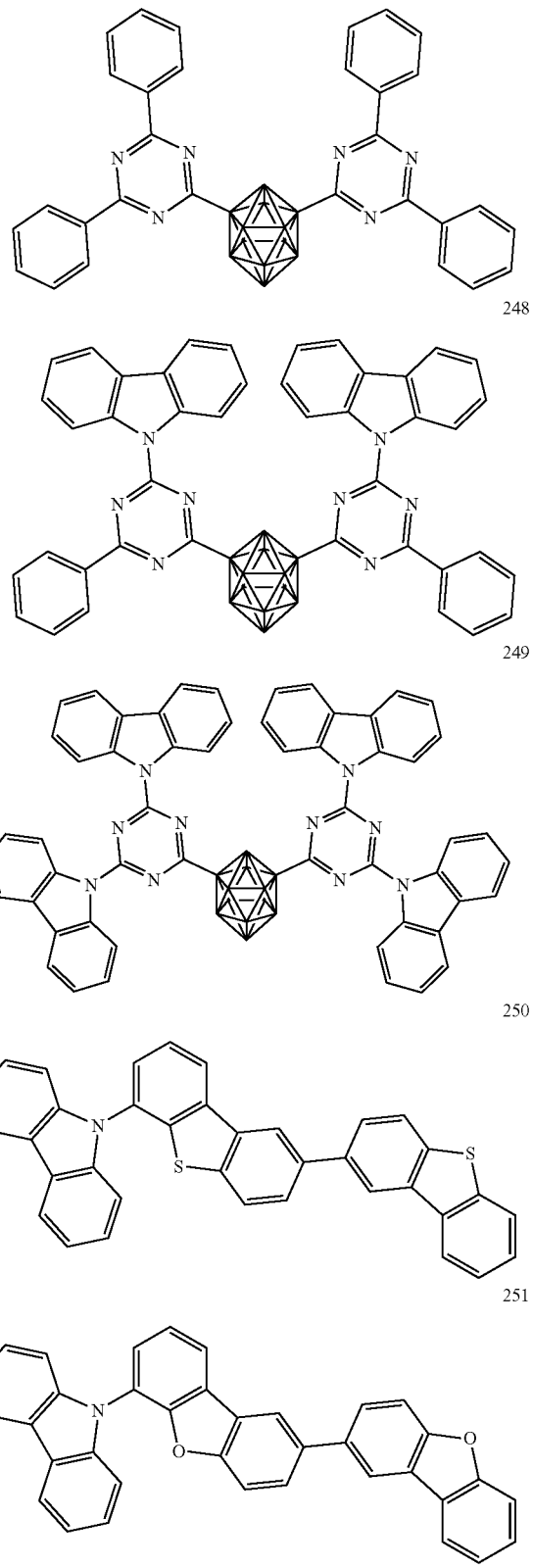

The presence of the light-emitting layer containing the TADF material selected from the compounds each represented by the general formula (1) can provide an organic EL device capable of delayed fluorescent light emission. In addition, the presence of the light-emitting layer containing the TADF material as a dopant material and containing the host material selected from the compounds each represented by the general formula (9) can provide an organic EL device having a more excellent characteristic. Further, the incorporation of two or more kinds of host materials can improve the characteristic. When two kinds of hosts are incorporated, at least one kind thereof is desirably a host material selected from the compounds each represented by the general formula (9). The first host is preferably a compound represented by the general formula (9). The second host may be a compound represented by the general formula (9) or may be any other host material. However, the second host is preferably a compound represented by the general formula (9).

Next, the structure of the organic EL device of the present invention is described with reference to the drawings. However, the structure of the organic EL device of the present invention is not limited thereto.

FIG. 1 is a sectional view for illustrating a structure example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may include an exciton-blocking layer adjacent to the light-emitting layer, or may include an electron-blocking layer between the light-emitting layer and the hole-injecting layer. The exciton-blocking layer may be inserted on any of the cathode side and the anode side of the light-emitting layer, and may also be inserted simultaneously on both sides. The organic EL device of the present invention includes the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. The hole-injecting/transporting layer means any one or both of the hole-injecting layer and the hole-transporting layer, and the electron-injecting/transporting layer means any one or both of an electron-injecting layer and the electron-transporting layer.

It is possible to adopt a reverse structure as compared to FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated as required.

Substrate

The organic EL device of the present invention is preferably supported by a substrate. The substrate is not particularly limited, and any substrate that has been conventionally used for an organic EL device may be used. For example, a substrate made of glass, a transparent plastic, quartz, or the like may be used.

Anode

A material formed of a metal, an alloy, an electrically conductive compound, or a mixture thereof, which has a large work function (4 eV or more), is preferably used as an anode material in the organic EL device. Specific examples of such electrode material include metals, such as Au, and conductive transparent materials, such as CuI, indium tin oxide (ITO), SnO$_2$, and ZnO. In addition, it may be possible to use an amorphous material, such as IDIXO (In$_2$O$_3$—ZnO), which may be used for manufacturing a transparent conductive film. In order to produce the anode, it may be possible to form any of those electrode materials into a thin film by using a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode materials is subjected to vapor deposition or sputtering. Alternatively, when a coatable substance, such as an organic conductive compound, is used, it is also possible to use a wet film-forming method, such as a printing method or a coating method. When luminescence is taken out from the anode, the transmittance of the anode is desirably controlled to more than 10%. In addition, the sheet resistance as the anode is preferably several hundred Ω/□ or less. The thickness of the film is, depending on its material, selected from usually the range of from 10 nm to 1,000 nm, preferably the range of from 10 nm to 200 nm.

In addition, after any of the above-mentioned metals is formed into a film having a thickness of from 1 nm to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and the cathode have transparency.

Light-Emitting Layer

The light-emitting layer is a layer that emits light after the production of an exciton by the recombination of a hole injected from the anode and an electron injected from the cathode. In the light-emitting layer, the TADF material represented by the general formula (1) may be used alone, or the TADF material may be used together with a host material. When the TADF material is used together with the host material, the TADF material serves as an organic light-emitting dopant material.

In addition, two or more kinds of compounds each represented by the general formula (1) may be used as TADF materials. Further, any other TADF material except the compound represented by the general formula (1) or an organic light-emitting dopant material may be used to the extent that the effect of the present invention is not impaired.

Examples of the organic light-emitting dopant material include fluorescent light-emitting dopants each formed of an aromatic hydrocarbon compound, such as a pyrene compound or an anthracene compound. Examples of the other TADF light-emitting dopant include: a metal complex, such as a tin complex or a copper complex; an indolocarbazole compound described in WO 2011/070963 A1; a cyanobenzene compound described in Nature 2012, 492, p. 234; and a carbazole compound.

Only one kind of organic light-emitting dopant material may be incorporated into the light-emitting layer, or two or more kinds of organic light-emitting dopant materials may be incorporated thereinto. The content of the TADF material or the organic light-emitting dopant material is preferably from 0.1 wt % to 50 wt %, more preferably from 1 wt % to 40 wt % with respect to the host material.

A dopant to be used in a phosphorescent light-emitting organic EL device, such as an Ir complex, is not used in the organic EL device of the present invention because the organic EL device of the present invention utilizes delayed fluorescent light emission.

Although a known host material to be used in a phosphorescent light-emitting device or a fluorescent light-emitting device may be used as the host material in the light-emitting layer, a carbazole compound represented by the general formula (9) is preferably used. In addition, a plurality of kinds of host materials may be used in combination. When the plurality of kinds of host materials are used in combination, at least one kind of host material is preferably selected from the carbazole compounds.

The known host material that may be used is a compound having a hole-transporting ability or an electron-transporting ability, and having a high glass transition temperature, and preferably has a S1 larger than the T1 of the TADF material or the light-emitting dopant material.

Such other host material is made public by many patent literatures and the like, and hence may be selected from the literatures and the like. The host material is not particularly limited, and specific examples thereof include an indole derivative, a carbazole derivative, an indolocarbazole derivative, a triazole derivative, an oxazole derivative, an oxadiazole derivative, an imidazole derivative, a phenylenediamine derivative, an arylamine derivative, a styrylanthracene derivative, a fluorenone derivative, a stilbene derivative, a triphenylene derivative, a carborane derivative, a porphyrin derivative, a phthalocyanine derivative, various metal complexes typified by a metal complex of an 8-quinolinol derivative, metal phthalocyanine, and a metal complex of a benzoxazole or benzothiazole derivative, and polymer compounds, such as a poly(N-vinylcarbazole) derivative, an aniline-based copolymer, a thiophene oligomer, a polythiophene derivative, a polyphenylene derivative, a polyphenylene vinylene derivative, and a polyfluorene derivative.

When a plurality of kinds of host materials are used, the respective host materials may be vapor-deposited from different deposition sources, or the plurality of kinds of hosts may be simultaneously vapor-deposited from one deposition source by preliminarily mixing the hosts before the vapor deposition to provide a preliminary mixture.

Injecting Layer

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

Hole-Blocking Layer

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole in the light-emitting layer by blocking holes while transporting electrons.

Although a known hole-blocking material may be used in the hole-blocking layer, the compound represented by the general formula (9) is preferably used. In addition, a plurality of kinds of hole-blocking materials may be used in combination.

Electron-Blocking Layer

The electron-blocking layer has, in a broad sense, the function of a hole-transporting layer, and is capable of improving the probability of recombining an electron and a hole in the light-emitting layer by blocking electrons while transporting holes.

Although a known electron-blocking layer material may be used as a material for the electron-blocking layer, the carbazole compound represented by the general formula (9) is preferably used. The thickness of the electron-blocking layer is preferably from 3 nm to 100 nm, more preferably from 5 nm to 30 nm.

Exciton-Blocking Layer

The exciton-blocking layer refers to a layer for blocking excitons produced by the recombination of a hole and an electron in the light-emitting layer from diffusing into charge-transporting layers. The insertion of this layer enables efficient confinement of the excitons in the light-emitting layer, thereby being able to improve the luminous efficiency of the device. In a device in which two or more light-emitting layers are adjacent to each other, the exciton-blocking layer may be inserted between two adjacent light-emitting layers.

Although a known exciton-blocking layer material may be used as a material for the exciton-blocking layer, the compound represented by the general formula (9) is preferably used.

A layer adjacent to the light-emitting layer is, for example, the hole-blocking layer, the electron-blocking layer, or the exciton-blocking layer. However, when none of those layers is arranged, the hole-transporting layer, the electron-transporting layer, or the like is the adjacent layer. The Cz compound represented by the general formula (9) is preferably used in at least one of the two adjacent layers.

Hole-Transporting Layer

The hole-transporting layer is formed of a hole-transporting material having a function of transporting holes, and a single hole-transporting layer or a plurality of hole-transporting layers may be formed.

The hole-transporting material has a hole-injecting property or a hole-transporting property or has an electron-blocking property, and any of an organic material and an inorganic material may be used as the hole-transporting material. Any compound selected from conventionally known compounds may be used for the hole-transporting layer. Examples of such hole-transporting material include a porphyrin derivative, an arylamine derivative, a triazole derivative, an oxadiazole derivative, an imidazole derivative, a polyarylalkane derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. Of those, a porphyrin derivative, an arylamine derivative, or a styrylamine derivative is preferably used, and an arylamine compound is more preferably used.

Electron-Transporting Layer

The electron-transporting layer is formed of a material having a function of transporting electrons, and a single electron-transporting layer or a plurality of electron-transporting layers may be formed.

An electron-transporting material (which also serves as a hole-blocking material in some cases) only needs to have a function of transferring electrons injected from the cathode into the light-emitting layer. Any compound selected from conventionally known compounds may be used for the electron-transporting layer. Examples thereof include a polycyclic aromatic derivative, such as naphthalene, anthracene, or phenanthroline, a tris(8-quinolinolato)aluminum (III) derivative, a phosphine oxide derivative, a nitro-substituted fluorene derivative, a diphenylquinone derivative, a thiopyran dioxide derivative, a carbodiimide, a fluorenylidenemethane derivative, anthraquinodimethane and anthrone derivatives, a bipyridine derivative, a quinoline derivative, an oxadiazole derivative, a benzimidazole derivative, a benzothiazole derivative, and an indolocarbazole derivative. Further, it is also possible to use a polymer material in which any of those materials is introduced in a polymer chain or is used as a polymer main chain.

A method of producing each layer at the time of the production of the organic EL device of the present invention is not particularly limited, and the layer may be produced by any one of a dry process and a wet process.

EXAMPLES

The present invention is hereinafter described in more detail by way of Examples. However, the present invention is not limited to Examples below.

Compounds used in Examples and Comparative Examples are shown below.

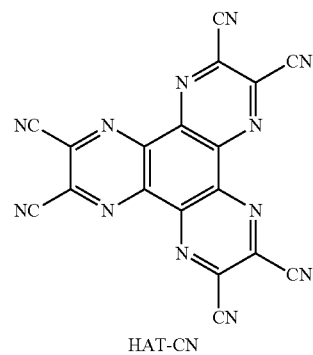

HAT-CN

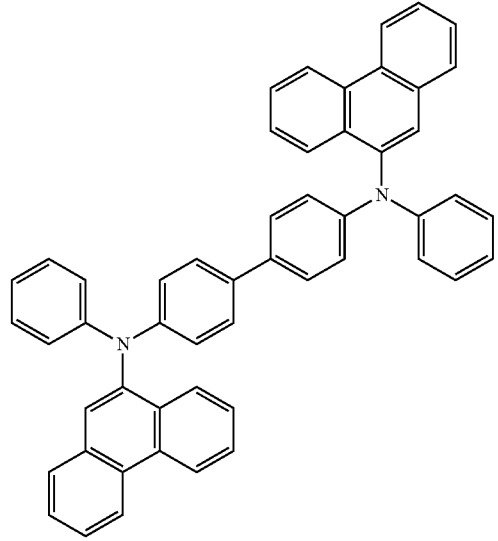

HT-1

-continued
HT-2
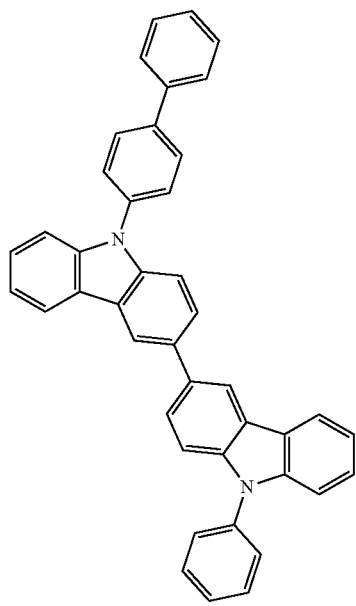
ET-1
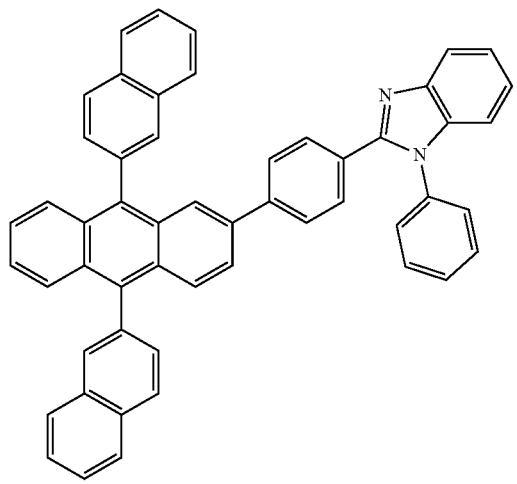
mCP
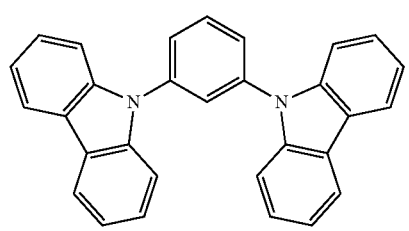
-continued
TD-1
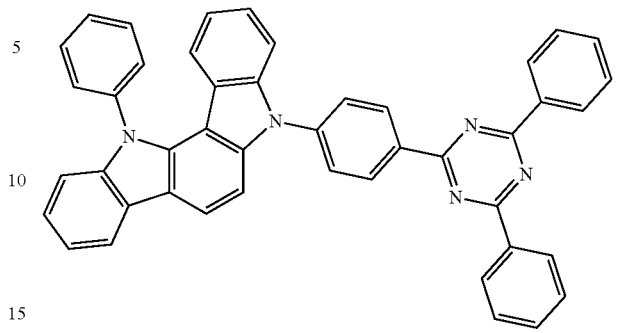
TD-2
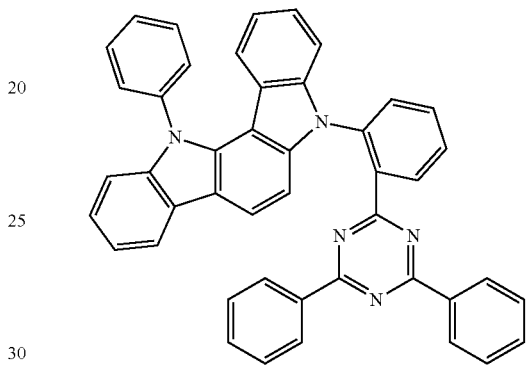
TD-3
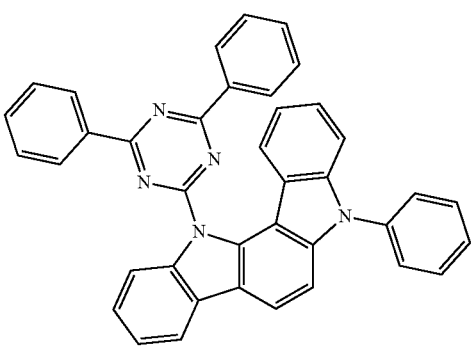
TD-4
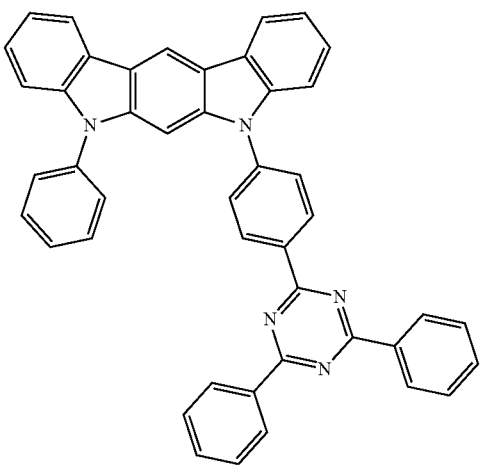

TD-5

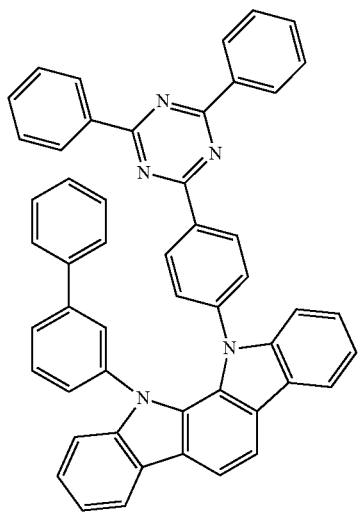

TD-6

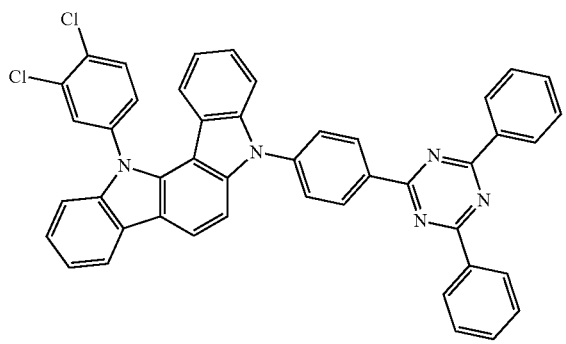

The S1 and T1 of each of Compounds 104, 114, 115, 129, and 148, and TD-1 to TD-6 described in the foregoing were measured. Further, the S1 and T1 of each of Compounds 212, 217, 238, and 243, and mCP described in the foregoing were measured.

The results are shown in Table 1.

The S1 and the T1 are measured as described below.

A sample compound is vapor-deposited onto a quartz substrate by a vacuum deposition method under the condition of a degree of vacuum of $10^{-4}$ Pa or less to form a deposited film having a thickness of 100 nm. The S1 is calculated by: measuring the emission spectrum of the deposited film; drawing a tangent to the rise-up of the emission spectrum at shorter wavelengths; and substituting a wavelength value λedge [nm] of the point of intersection of the tangent and the axis of abscissa of the spectrum into the following equation (i).

$$S1\ [\text{eV}] = 1{,}239.85/\lambda\text{edge} \quad \text{(i)}$$

The T1 is calculated by: measuring the phosphorescence spectrum of the deposited film; drawing a tangent to the rise-up of the phosphorescence spectrum at shorter wavelengths; and substituting a wavelength value λedge [nm] of the point of intersection of the tangent and the axis of abscissa of the spectrum into the equation (ii).

$$T1\ [\text{eV}] = 1{,}239.85/\lambda\text{edge} \quad \text{(ii)}$$

TABLE 1

| Compound | S1 (eV) | T1 (eV) | S1-T1 (eV) |
|---|---|---|---|
| 104 | 3.0 | 2.9 | 0.2 |
| 114 | 2.8 | 2.8 | 0.0 |
| 115 | 3.0 | 2.9 | 0.1 |
| 129 | 2.9 | 2.7 | 0.2 |
| 148 | 3.0 | 2.8 | 0.2 |
| TD-1 | 2.9 | 2.7 | 0.2 |
| TD-2 | 2.7 | 2.7 | 0.0 |
| TD-3 | 2.9 | 2.9 | 0.0 |
| TD-4 | 2.8 | 2.6 | 0.2 |
| TD-5 | 2.9 | 2.7 | 0.2 |
| TD-6 | 3.0 | 2.8 | 0.2 |
| 212 | 3.5 | 2.9 | 0.6 |
| 217 | 3.6 | 3.1 | 0.5 |
| 238 | 3.4 | 3.1 | 0.3 |
| 243 | 3.7 | 3.1 | 0.6 |
| mCP | 3.7 | 3.1 | 0.6 |

Experiment Example 1

The fluorescence lifetime of Compound 104 was measured. Compound 104 and Compound 243 were vapor-deposited from different deposition sources onto a quartz substrate by a vacuum deposition method under the condition of a degree of vacuum of $10^{-4}$ Pa or less to form a co-deposited film having a thickness of 100 nm in which the concentration of Compound 104 was 30 wt %. The emission spectrum of the thin film was measured and light emission having a peak at 481 nm was observed. In addition, the emission lifetime of the compound was measured with a small fluorescence lifetime-measuring apparatus (Quantaurus-tau manufactured by Hamamatsu Photonics K.K.) under a nitrogen atmosphere. Fluorescence having an excitation lifetime of 11 ns and delayed fluorescence having an excitation lifetime of 12 μs were observed, and hence it was confirmed that Compound 104 was a compound showing delayed fluorescent light emission.

In addition, the fluorescence lifetime of Compound 243 was measured. Compound 243 was vapor-deposited onto a quartz substrate by a vacuum deposition method under the condition of a degree of vacuum of $10^{-4}$ Pa or less to form a deposited film having a thickness of 100 nm. The emission spectrum of the thin film was measured, and light emission having a peak at 389 nm was observed. In addition, the emission lifetime of the compound was measured in the same manner as that described above. Only fluorescence having an excitation lifetime of 3 ns was observed, and hence it was confirmed that Compound 243 was a compound that did not show delayed fluorescent light emission.

The fluorescence lifetimes of Compounds 114, 115, 129, and 148 were also each measured in the same manner as in Experiment Example 1. As a result, delayed fluorescence was observed, and hence it was confirmed that the compounds were materials each showing delayed fluorescent light emission. In addition, the fluorescence lifetime of Compound TD-1 was measured in the same manner as in Experiment Example 1. As a result, delayed fluorescence was observed, and hence it was confirmed that the compound was a material showing delayed fluorescent light emission.

Example 1

Each thin film was laminated on a glass substrate having formed thereon an anode formed of ITO having a thickness of 70 nm by a vacuum deposition method at a degree of vacuum of 4.0×10$^{-5}$ Pa. First, HAT-CN serving as a hole-injecting layer was formed on ITO so as to have a thickness of 10 nm, and then HT-1 serving as a hole-transporting layer was formed so as to have a thickness of 25 nm. Next, Compound (217) serving as an electron-blocking layer was formed so as to have a thickness of 5 nm. Then, Compound (243) serving as a host and Compound (104) serving as a dopant were respectively co-deposited from different deposition sources to form a light-emitting layer having a thickness of 30 nm. At this time, the co-deposition was performed under such a deposition condition that the concentration of Compound (104) became 30 wt %. Next, Compound (238) serving as a hole-blocking layer was formed so as to have a thickness of 5 nm. Next, ET-1 serving as an electron-transporting layer was formed so as to have a thickness of 40 nm. Further, lithium fluoride (LiF) serving as an electron-injecting layer was formed on the electron-transporting layer so as to have a thickness of 1 nm. Finally, aluminum (Al) serving as a cathode was formed on the electron-injecting layer so as to have a thickness of 70 nm. Thus, an organic EL device was produced.

Examples 2 to 6 and Comparative Examples 1 to 5

Organic EL devices were each produced in the same manner as in Example 1 except that the dopant and the host were changed to compounds shown in Table 2.

Examples 7 and 8 and Comparative Examples 6 to 8

Organic EL devices were each produced in the same manner as in Example 1 except that the electron-blocking layer, the host, and the hole-blocking layer were changed to compounds shown in Table 2.

Example 9

Each thin film was laminated on a glass substrate having formed thereon an anode formed of ITO having a thickness of 70 nm by a vacuum deposition method at a degree of vacuum of 4.0×10$^{-5}$ Pa. First, HAT-CN serving as a hole-injecting layer was formed on ITO so as to have a thickness of 10 nm, and then HT-1 serving as a hole-transporting layer was formed so as to have a thickness of 25 nm. Next, Compound (217) serving as an electron-blocking layer was formed so as to have a thickness of 5 nm. Next, Compound (243) serving as a host, Compound (238) serving as a second host, and Compound (104) serving as a dopant were respectively co-deposited from different deposition sources to form a light-emitting layer having a thickness of 30 nm. At this time, the co-deposition was performed under such a deposition condition that the concentration of Compound (104) became 15 wt % and the weight ratio between the host and the second host became 50:50. Next, Compound (238) serving as a hole-blocking layer was formed so as to have a thickness of 5 nm. Next, ET-1 serving as an electron-transporting layer was formed so as to have a thickness of 40 nm. Further, lithium fluoride (LiF) serving as an electron-injecting layer was formed on the electron-transporting layer so as to have a thickness of 1 nm. Finally, aluminum (Al) serving as a cathode was formed on the electron-injecting layer so as to have a thickness of 70 nm. Thus, an organic EL device was produced.

The compounds used as the dopants, the hosts, the second host, the hole-blocking layers, and the electron-blocking layers are shown in Table 2.

TABLE 2

| | Dopant | Host | Second host | Hole-blocking layer | Electron-blocking layer |
|---|---|---|---|---|---|
| Ex. 1 | 104 | 243 | — | 238 | 217 |
| Ex. 2 | 114 | 217 | — | 238 | 217 |
| Ex. 3 | 115 | 238 | — | 238 | 217 |
| Ex. 4 | 129 | 243 | — | 238 | 217 |
| Ex. 5 | 148 | 212 | — | 238 | 217 |
| Ex. 6 | 104 | mCP | — | 238 | 217 |
| Ex. 7 | 104 | 243 | — | ET-1 | 217 |
| Ex. 8 | 104 | 243 | — | 238 | HT-2 |
| Ex. 9 | 104 | 243 | 238 | 238 | 217 |
| Comp. Ex. 1 | TD-1 | 243 | — | 238 | 217 |
| Comp. Ex. 2 | TD-2 | 217 | — | 238 | 217 |
| Comp. Ex. 3 | TD-3 | 243 | — | 238 | 217 |
| Comp. Ex. 4 | TD-4 | 212 | — | 238 | 217 |
| Comp. Ex. 5 | TD-5 | 238 | — | 238 | 217 |
| Comp. Ex. 6 | TD-1 | 243 | — | ET-1 | 217 |
| Comp. Ex. 7 | TD-1 | 243 | — | 238 | HT-2 |
| Comp. Ex. 8 | TD-6 | 243 | — | 238 | 217 |

The maximum emission wavelengths of the emission spectra of the produced organic EL devices, and the external quantum efficiencies and lifetimes of the devices are shown in Table 3. The maximum emission wavelengths and the external quantum efficiencies are values at a driving current density of 2.5 mA/cm$^2$, and are initial characteristics. The lifetimes were each obtained by measuring a time period required for a luminance to attenuate from an initial luminance of 500 cd/m$^2$ to 95% of the initial luminance.

TABLE 3

| | Maximum emission wavelength (nm) | External quantum efficiency (%) | Lifetime (h) |
|---|---|---|---|
| Ex. 1 | 471 | 16.1 | 104 |
| Ex. 2 | 489 | 20.5 | 343 |
| Ex. 3 | 499 | 8.2 | 84 |
| Ex. 4 | 479 | 12.1 | 92 |
| Ex. 5 | 469 | 11.4 | 78 |
| Ex. 6 | 473 | 14.2 | 33 |
| Ex. 7 | 470 | 8.3 | 82 |
| Ex. 8 | 469 | 5.5 | 199 |
| Ex. 9 | 475 | 15.8 | 188 |
| Comp. Ex. 1 | 483 | 15.6 | 81 |
| Comp. Ex. 2 | 501 | 20.0 | 319 |
| Comp. Ex. 3 | 516 | 5.7 | 48 |
| Comp. Ex. 4 | 491 | 11.0 | 69 |
| Comp. Ex. 5 | 474 | 10.7 | 40 |
| Comp. Ex. 6 | 481 | 8.9 | 66 |
| Comp. Ex. 7 | 479 | 5.3 | 158 |
| Comp. Ex. 8 | 477 | 15.8 | 19 |

As can be seen from Table 3, an organic EL device using, as a light-emitting dopant, a TADF material represented by the general formula (1), the material having at least one fluorine atom as a substituent, has an emission wavelength at shorter wavelengths, and has a more excellent lifetime characteristic as compared to the case where a TADF material free of any fluorine substituent is used as a light-emitting dopant. This is probably because the introduction of a fluorine substituent reduced the HOMO energy level of the former material to increase a gap between the HOMO and LUMO energies thereof, thereby shortening the emission wavelength thereof. That is also probably because the reduc-

The invention claimed is:

1. An organic electroluminescent device, comprising one or more light-emitting layers between an anode and a cathode opposite to each other, wherein at least one of the light-emitting layers contains a compound represented by any one of the following general formulae (3), (4) and (7) as a thermally activated delayed fluorescent light-emitting material and a host material:

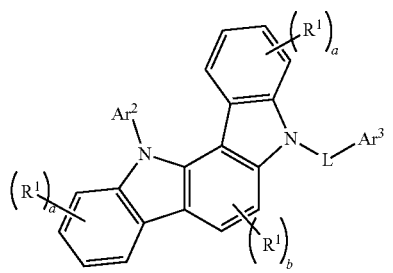

(3)

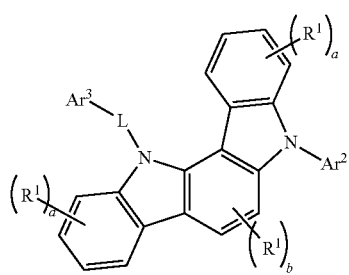

(4)

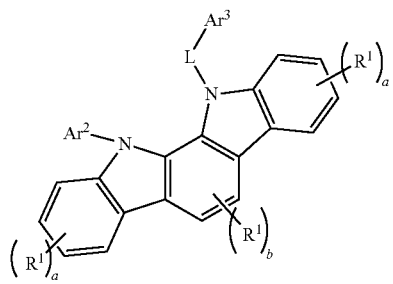

(7)

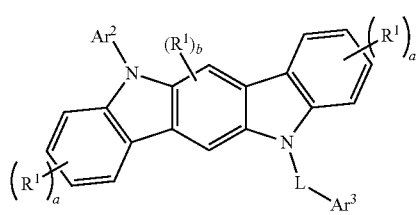

(8)

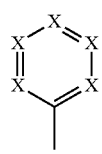

(3b)

where:

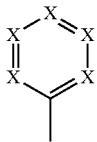

(3b)

Ar² represents a substituted or unsubstituted aromatic hydrocarbon group having 6 to 30 carbon atoms, a substituted or unsubstituted aromatic heterocyclic group having 3 to 17 carbon atoms, or a linked aromatic group formed by linking 2 to 6 aromatic rings of aromatic groups each selected from the aromatic hydrocarbon group and the aromatic heterocyclic group, the aromatic hydrocarbon group, the aromatic heterocyclic group, and the linked aromatic group each having 1 to 2 fluorine atoms, wherein the fluorine atom is bonded to a carbon atom comprising the aromatic ring;

L represents a single bond, a substituted or unsubstituted aromatic hydrocarbon group having 6 to 12 carbon atoms, or a substituted or unsubstituted aromatic heterocyclic group having 3 to 10 carbon atoms;

Ar³ represents a heterocyclic group represented by the formula (3b), Xs each represent CR² or N, and at least one of Xs represents N;

R¹s each independently represent an aliphatic hydrocarbon group having 1 to 10 carbon atoms, a substituted or unsubstituted diarylamino group having 12 to 44 carbon atoms, a substituted or unsubstituted aromatic hydrocarbon group having 6 to 18 carbon atoms, or a substituted or unsubstituted aromatic heterocyclic group having 3 to 17 carbon atoms;

R² represents hydrogen, an aliphatic hydrocarbon group having 1 to 10 carbon atoms, a substituted or unsubstituted aromatic hydrocarbon group having 6 to 18 carbon atoms, a substituted or unsubstituted aromatic heterocyclic group having 3 to 10 carbon atoms, or a linked aromatic group formed by linking 2 to 4 aromatic rings of aromatic groups each selected from the aromatic hydrocarbon group and the aromatic heterocyclic group;

when Ar² represents a linked aromatic group, the aromatic rings to be linked may be identical to or different from each other, and the linked aromatic group may be linear or branched; and "a" represents an integer of from 0 to 4, and "b" represents an integer of from 0 to 2;

wherein the host material is a compound represented by the following general formula (9):

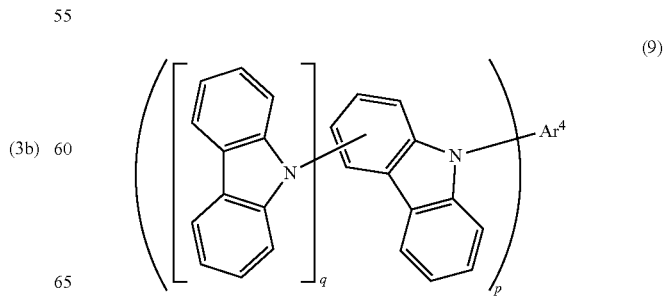

(9)

where Ar⁴ represents a p-valent group, which may have a substituent and is produced from benzene, a nitrogen-containing six-membered heterocyclic compound, dibenzofuran, dibenzothiophene, carbazole, carborane, or a linked compound obtained by linking 2 to 4 of the compounds, "p" represents an integer of 1 or 2, and "q" represents an integer of from 0 to 4, and when Ar⁴ represents a p-valent group produced from benzene, "q" represents an integer of from 1 to 4.

2. The organic electroluminescent device according to claim 1, wherein Ar² represents a substituted phenyl group, or a substituted biphenyl group, the groups each having 1 to 2 fluorine atoms.

3. The organic electroluminescent device according to claim 1, wherein L represents a substituted or unsubstituted aromatic hydrocarbon group having 6 to 12 carbon atoms.

4. The organic electroluminescent device according to claim 1, wherein a difference between an excited singlet energy (S1) and an excited triplet energy (T1) of the thermally activated delayed fluorescent light-emitting material is 0.2 eV or less.

5. The organic electroluminescent device according to claim 1, wherein the light-emitting layer contains at least two kinds of compounds each represented by the general formula (9) as the host materials.

6. The organic electroluminescent device according to claim 1, wherein the host material has an excited triplet energy (T1) larger than an excited singlet energy (S1) of the thermally activated delayed fluorescent material.

7. The organic electroluminescent device according to claim 1, wherein the compound represented by the general formula (9) is incorporated into a layer adjacent to the light-emitting layer.

8. The organic electroluminescent device according to claim 1, wherein L represents a single bond, a phenyl group substituted with one fluorine atom, a phenyl group substituted with two fluorine atoms, or a phenyl group substituted with four fluorine atoms.

9. The organic electroluminescent device according to claim 1, wherein p represents an integer of 1 and q represents an integer of 1.

10. An organic electroluminescent device, comprising one or more light-emitting layers between an anode and a cathode opposite to each other, wherein at least one of the light-emitting layers contains a compound represented by any one of the following general formulae (3) to (7) as a thermally activated delayed fluorescent light-emitting material and a host material:

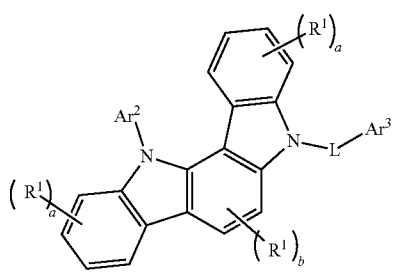

(3)

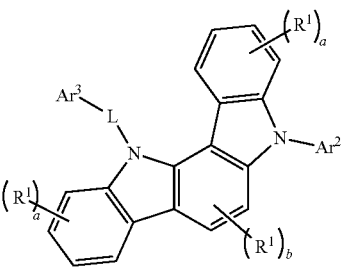

(4)

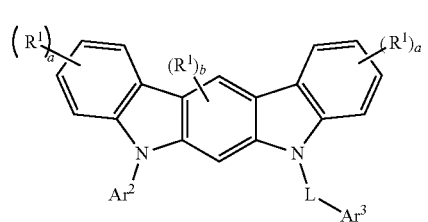

(5)

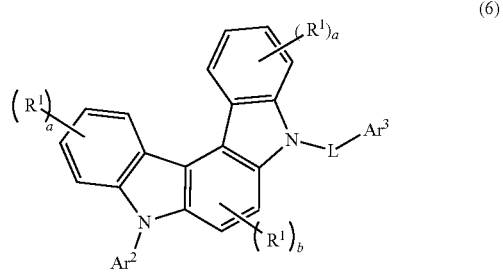

(6)

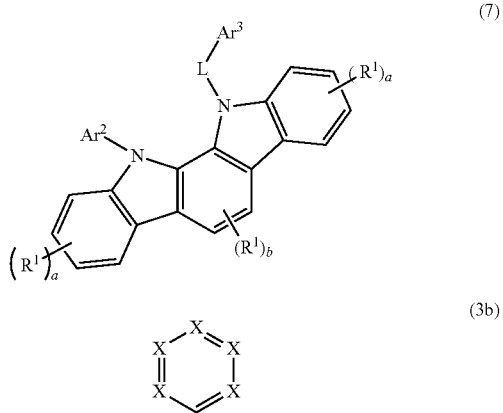

(7)

(3b)

where:
Ar² represents a substituted or unsubstituted aromatic hydrocarbon group having 6 to 30 carbon atoms, a substituted or unsubstituted aromatic heterocyclic group having 3 to 17 carbon atoms, or a linked aromatic group formed by linking 2 to 6 aromatic rings of aromatic groups each selected from the aromatic hydrocarbon group and the aromatic heterocyclic group, the aromatic hydrocarbon group, the aromatic heterocyclic group, and the linked aromatic group each having 1 to 2 fluorine atoms, wherein the fluorine atom is bonded to a carbon atom comprising the aromatic ring;

L represents a single bond or a substituted or unsubstituted phenyl;

Ar³ represents a heterocyclic group represented by the formula (3b), Xs each represent $CR^2$ or N, and at least one of Xs represents N;

$R^1$s each independently represent an aliphatic hydrocarbon group having 1 to 10 carbon atoms;

$R^2$ represents hydrogen, an aliphatic hydrocarbon group having 1 to 10 carbon atoms, a substituted or unsubstituted aromatic hydrocarbon group having 6 to 18 carbon atoms, a substituted or unsubstituted aromatic heterocyclic group having 3 to 10 carbon atoms, or a linked aromatic group formed by linking 2 to 4 aromatic rings of aromatic groups each selected from the aromatic hydrocarbon group and the aromatic heterocyclic group;

when $Ar^2$ represents a linked aromatic group, the aromatic rings to be linked may be identical to or different from each other, and the linked aromatic group may be linear or branched; and "a" represents an integer of 0, and "b" represents an integer of 0;

wherein the host material is a compound represented by the following general formula (9):

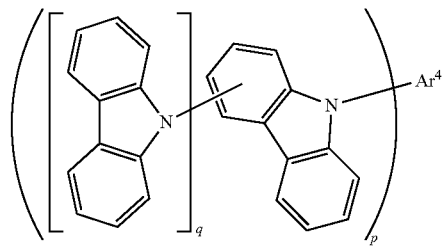

(9)

where $Ar^4$ represents a p-valent group, which may have a substituent and is produced from benzene, dibenzofuran, dibenzothiophene, carborane, or a linked compound obtained by linking 2 to 4 of the compounds, "p" represents an integer of 1 or 2, and "q" represents an integer of from 0 to 4, and when $Ar^4$ represents a p-valent group produced from benzene, "q" represents an integer of from 1 to 4;

wherein a difference between an excited singlet energy (S1) and an excited triplet energy (T1) of the thermally activated delayed fluorescent light-emitting material is 0.2 eV or less; and wherein the host material has an excited triplet energy (T1) larger than an excited singlet energy (S1) of the thermally activated delayed fluorescent material.

* * * * *